US008999401B2

(12) United States Patent
Luria et al.

(10) Patent No.: US 8,999,401 B2
(45) Date of Patent: Apr. 7, 2015

(54) DELIVERY SYSTEM AND METHOD TO DELIVER HOMEOPATHIC COMPLEXES COMPRISING HOMEOPATHIC COLORED PIGMENT PRODUCTS FOR COSMETIC USE

(76) Inventors: Henry Steven Luria, Boulder, CO (US); Joy Elizabeth Luria, Boulder, CO (US)

(*) Notice: Subject to any disclaimer, the term of this patent is extended or adjusted under 35 U.S.C. 154(b) by 1282 days.

(21) Appl. No.: 12/062,083

(22) Filed: Apr. 3, 2008

(65) Prior Publication Data

US 2008/0279902 A1  Nov. 13, 2008

Related U.S. Application Data

(60) Provisional application No. 60/928,404, filed on May 9, 2007.

(51) Int. Cl.

| | |
|---|---|
| A61K 36/00 | (2006.01) |
| A61K 35/64 | (2006.01) |
| A61K 8/02 | (2006.01) |
| A61K 33/26 | (2006.01) |
| A61K 33/00 | (2006.01) |
| A61K 33/06 | (2006.01) |
| A61K 33/24 | (2006.01) |
| A61K 33/30 | (2006.01) |
| A61Q 1/02 | (2006.01) |
| A61Q 1/04 | (2006.01) |
| A61Q 1/06 | (2006.01) |
| A61Q 1/10 | (2006.01) |
| A61Q 1/12 | (2006.01) |
| A61Q 17/04 | (2006.01) |
| A61Q 19/00 | (2006.01) |
| A61Q 19/08 | (2006.01) |

(52) U.S. Cl.
CPC . *A61K 33/26* (2013.01); *A61K 8/02* (2013.01); *A61K 33/00* (2013.01); *A61K 33/06* (2013.01); *A61K 33/24* (2013.01); *A61K 33/30* (2013.01); *A61K 36/00* (2013.01); *A61K 2800/28* (2013.01); *A61K 2800/42* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 17/04* (2013.01); *A61Q 19/00* (2013.01); *A61Q 19/001* (2013.01); *A61Q 19/005* (2013.01); *A61Q 19/08* (2013.01)

(58) Field of Classification Search
USPC .................................. 424/725, 401
See application file for complete search history.

(56) References Cited

U.S. PATENT DOCUMENTS

| | | | | |
|---|---|---|---|---|
| 4,163,049 | A | * | 7/1979 | Aubin ........................... 424/539 |
| 5,641,509 | A | | 6/1997 | Gross et al. |
| 5,653,984 | A | * | 8/1997 | Fodor et al. ................... 424/776 |
| 5,795,573 | A | * | 8/1998 | Paradise ........................ 424/737 |
| 6,238,677 | B1 | * | 5/2001 | Fanta et al. ................... 424/400 |
| 6,569,439 | B1 | | 5/2003 | Stier |
| 2006/0153889 | A1 | * | 7/2006 | Friel et al. ..................... 424/401 |
| 2006/0210501 | A1 | * | 9/2006 | Benard et al. .................. 424/63 |
| 2009/0081262 | A1 | * | 3/2009 | Toledano et al. ............. 424/401 |

FOREIGN PATENT DOCUMENTS

| | | | | |
|---|---|---|---|---|
| DE | 102005021382 | A1 | * | 10/2006 |
| JP | 08-12566 | | * | 1/1996 |
| JP | 09-077638 | | * | 3/1997 |
| JP | 11-349469 | A | * | 12/1999 |
| KR | 567403 | B1 | * | 4/2006 |

OTHER PUBLICATIONS

Derwent Acc. No. 2006-697939, "Agent, useful to treat and prevent skin diseases", Oct. 18, 2006, abstract of DE 102005021382 A1.*
Kuroda, A. et al., "Ultraviolet-shielding cosmetic", JP 411349469 A, Dec. 21, 1999, abstract.*
Suzuki, M. et al., "Foundation for cosmetic", JP409077638A, Mar. 25, 1997, abstract.*
Komazaki, H. et al. "Inhibitor for tyrosinase activity", JP 08-012566, Jan. 16, 1996, raw translation.*
Kim, D., Dec. 16, 2002, Derwent Acc. No. 2003-178484, English abstract of KR 2002093655 A and KR 507403 B1.*
Nechaeva, N., Feb. 27, 2000, Derwent Acc. No. 2000-645587, English abstract of RU 2145865 C1.*
Dermaxine (Pty) Ltd. *Centella asiatica.* Sep. 18, 2005 (online) [retreived on Jun. 20, 2008] Retrieved from the Internet: <URL: http://web.archive.org/web/20051001064824/www.dermaxime.com/centella-asiatica.htm>, pp. 1-3.
Enkueros Inc. Natra-Bio Acne Relief #526 Liquid 1 Oz. (Homeopathic Remedies). 2005 (online) [retreived on Jun. 24, 2008] Retrieved from the Internet: <URL: http://www.enkueros.net/371400526019.html>. p. 1, para 1, in 1-2, para 3.

(Continued)

*Primary Examiner* — Gina Justice
(74) *Attorney, Agent, or Firm* — Greenberg Traurig, LLP; Chinh H. Pham; Natalie Salem

(57) ABSTRACT

The present invention provides a delivery system and method to deliver topically homeopathic amounts of at least one Homeopathic Complex. It further provides a Homeopathic Colored Pigment Product containing a coloring agent having a plurality of particles having at least one surface and a homeopathically effective amount of at least one Homeopathic Complex, wherein the at least one surface of particles in the plurality of particles of the coloring agent contains the at least one Homeopathic Complex. It also provides cosmetic formulations containing the Homeopathic Colored Pigment Product for normal skin, problem skin, aged skin, and skin damaged by the harmful rays of the sun.

50 Claims, No Drawings

(56) References Cited

OTHER PUBLICATIONS

Beauty Bridge. Youngblood—Liquid Mineral Foundation. Feb. 18, 2007 (online) [retrieved on Jun. 23, 2008] Retrieved from the Internet: <URL: http://web.archive.org/web/20070218124429/http://www.beautybridge.com/yolimifo.html>, p. 1, para 1, p. 2, para 1.

Aiken Skincare. Polution Solution. 2005. (online) [retrieved on Jun. 23, 2008 ] Retrieved from the Internet: <URL: http://www.aikenskincare.us/index.php?main_page=product_info&products_id=29>. p. 1-2.

Plants for a Future. *Lycopodium clavatum*. 1997-2000 (online) [retrieved on Jun. 23, 2008 ]. Retrieved from the Internet: <URL: http://www.ibibio.org/pfaf/cgi-bin/arr_html?Lycopodium+clavatum>. p. 2, para 4-5, 9.

Russ Fons for California Cosmetics Corp. Overwhelming Response to "BioHexol" Prompts California Cosmetics to Add Propiertary Blend to More Products. Nov. 29, 2006 (online) [retrieved on Jun. 23, 2008 ] Retrieved from the Internet: <URL:http://www.expertclick.com/NewsReleaseWire/default.cfm?Action=ReleaseDetails&ID=14633>. p. 1, para 7; p. 2,para 3.

Bouncing Bear Botanicals. *Atropa belladonna*—Deadly Nightshade Seeds and Foliage for Sale. 2005 (online) [retrieved on Jun. 24, 2008 ] Retrieved from the Internet: <URL: http://web.archive.org/web/20051230015437/http://www.bouncingbearbotanicals.com/deadly-nightshade-p-105.html>. p. 1, para 4, in 1-2.

Clarke. A Dictionarry of Practical Materia Medica, China Officinalis. 1999 (online) [retrieved on Jun. 24, 2008)] Retrieved from the Internet: <URL:http://www.homeoint.org/books3/clark13/cluschin.htm>. p. 1, para 1; p. 6, para 2.

\* cited by examiner

DELIVERY SYSTEM AND METHOD TO DELIVER HOMEOPATHIC COMPLEXES COMPRISING HOMEOPATHIC COLORED PIGMENT PRODUCTS FOR COSMETIC USE

CROSS-REFERENCE TO RELATED APPLICATIONS

This application claims the benefit of U.S. Provisional Application Ser. No. 60/928,404 filed May 9, 2007, which is hereby incorporated by reference in its entirety.

FIELD OF THE INVENTION

The present invention relates to a delivery system and method to deliver topically homeopathic amounts of at least one Homeopathic Complex.

BACKGROUND OF THE INVENTION

Homeopathy is a system of medical practice that treats a disease, affliction or condition by the administration of minute doses of a remedy to a person suffering from that disease, affliction or condition to match the symptoms. Hahnemann's Law of Similars or "like cures like," holds that the use of a homeopathic substance will provide the healing properties to reduce or alleviate the symptoms or disease that its Mother Tincture would have caused if taken in its full potent form Homeopathic remedies have been considered drugs in the United States since 1897. There are many known homeopathic agents whose affects on the human body are known.

A subset of homeopathic elements exists, known as cell salts. It is understood in homeopathic medicine that if an imbalance were to occur in any of the twelve (12) Cell Salts essential to the human body, illness would follow. While many traditional homeopathic remedies work on the principle of "like cures like", the twelve (12) Cell Salts help the body to remedy deficiencies at their core, thereby healing, promoting wellness, and preventing disease, afflictions and medical conditions.

Homeopathic agents are largely delivered via oral solutions such as pellets, tablets, powders, and liquid drops, which are placed on or under the tongue. Pellets typically are formed from tiny sugar balls that have been saturated with the homeopathic liquid remedy. A dropper is used to place the drops on or under the tongue or in a small amount of drinking water.

A large number of homeopathic remedies, including both those that incorporate general homeopathic agents and those that incorporate some or all of the twelve (12) Cell Salts, are well-suited for therapeutic effect on skin of the human body. Skin conditions suitable for treatment with homeopathic remedies include viral, bacterial, fungal and parasitic conditions, allergic conditions, pain and pain management, aging, dark circles, puffiness, acute and chronic diseases, toxin removal, and trauma, including but not limited to, itching, acne, rosacea, eczema, pimples, psoriasis, hives, other dermatological eruptions, skin blisters, redness, poison ivy, poison oak, poison sumac, bug bites and stings, skin discolorations, skin tags, stretch marks, rashes, dryness, flaking, scars, and keloids.

Moreover, human skin benefits substantially from the regular use of the Twelve (12) Cell Salts, which prevent varicose and spider veins, acne and other skin eruptions and dryness of the skin.

Absorption of therapeutic homeopathic agents generally is increased when the time that the skin is exposed to homeopathic agents and/or the surface area of the skin exposed to the agents is increased.

As understood, there have been no efforts to date to deliver homeopathically effective amounts of homeopathic agents formulated as colored cosmetics.

The term "cosmetics" generally refers to (i) substances intended to be rubbed, poured, sprinkled or sprayed on, introduced or otherwise applied to the human body or other animal body or any part thereof for cleansing, beautifying, promoting attractiveness or altering the appearance, and (ii) substances intended for use as a component of any such substances, except that such term shall not include soap. Such products may be used to conceal symptoms of illness, affliction or medical conditions of the skin. Generally, such products may be applied to large surface areas of skin, to damaged skin, and to delicate areas of the skin, and are left on the skin for long periods of time.

A number of topical preparations that incorporate botanical ingredients have been described. For example, U.S. patent application 2004/0185123 A1 discloses a topical formulation comprising plant extracts and niacin to treat dry skin disorders. The formulation contains a combination of dry, aqueous, acid, and alcohol extracts of black walnut hull, wormwood, turmeric rhizome, garlic, chamomile, licorice root, *aloe vera*, niacin and herbal anti-bacterial agents. U.S. patent application 2007/0122492 discloses dermatological compositions comprising plant extracts that are capable of inhibiting one or more extracellular proteases. U.S. Pat. No. 6,800,292 B1 discloses compositions comprising fruit extracts, the most preferred of which is a pomegranate extract in an amount sufficient to neutralize free radicals useful to support the female reproductive system. The disclosed topical water-based compositions comprise at least one of *Pulsatilla, Berberis vulgaris*, Hepar sulphuris calcareum, *Lilium tigrinum, Hydrastis canadensis, Cantharis, Candida albicans, Sepia* and *Thuja occidentalis* for use as a personal lubricant.

None of these references disclose, teach or suggest the present invention, which employs coloring agents to deliver homeopathically effective amounts of Homeopathic Complexes to the skin of the face. The Homeopathic Colored Pigment Products of the present invention deliver the medicinal qualities of the homeopathic remedies while beautifying the skin.

SUMMARY OF THE INVENTION

The present invention provides a delivery system and method to deliver topically homeopathic amounts of at least one Homeopathic Complex. It further provides a Homeopathic Colored Pigment Product containing a coloring agent having a plurality of particles having at least one surface and a homeopathically effective amount of at least one Homeopathic Complex, wherein the at least one surface of the plurality of particles of the coloring agent contains the at least one Homeopathic Complex. It also provides cosmetic formulations containing the Homeopathic Colored Pigment Product for normal skin, problem skin, aged skin, and skin damaged by the harmful rays of the sun.

In one aspect of the present invention, a delivery system to deliver topically to a subject in need thereof a homeopathically effective amount of at least one Homeopathic Complex includes the homeopathically effective amount of the at least one Homeopathic Complex; and a coloring agent comprising a plurality of particles having at least one surface, wherein the at least one surface of the plurality of particles of the coloring agent comprises the at least one Homeopathic Complex. According to one embodiment of the delivery system, the delivery system is formulated into a cosmetic formulation. According to another embodiment, the cosmetic formulation is in the form of a foundation make-up. According to another embodiment, the cosmetic formulation is in the form of a blush make-up. According to another embodiment, the cosmetic formulation is in the form of an eye shadow make-up. According to another embodiment, the cosmetic formulation is in the form of a eye liner. According to another embodiment, the cosmetic formulation is in the form of a lip liner. According to another embodiment, the cosmetic formulation is in the form of a lipstick. According to another embodiment, the cosmetic formulation is in the form of a lip gloss. According to another embodiment, the cosmetic formulation is in the form of a nail polish. According to another embodiment, the cosmetic formulation is in the form of a sunscreen. According to another embodiment, the cosmetic formulation is in the form of a face cream or eye cream. According to another embodiment, the cosmetic formulation is in the form of a lotion. According to another embodiment, the cosmetic formulation is in the form of a facial serum. According to another embodiment, the cosmetic formulation is in the form of a facial scrub. According to another embodiment, the coloring agent of the delivery system is at least coloring agent selected from the group consisting of mica, titanium dioxide, iron oxide, ferric ferrocyanide, ultramarine blue, clay, starch, aloe powder, corn starch, arrowroot powder, and zinc oxide. According to another embodiment, the at least one Homeopathic Complex of the delivery system comprises at least two homeopathic agents selected from the group consisting of Calcarea fluorica-Fluor spar (Calcium fluoride), Calcarea phosphorica (Calcium phosphate), Calcarea sulphurica (Calcium sulfate), Ferrum phosphoricum (Iron phosphate), Kalium muriaticum (Potassium chloride), Kalium phosphoricum (Potassium phosphate), Kalium sulphuricum (Potassium sulfate), Magnesia phosphorica (Magnesium phosphate), Natrium muriaticum (Sodium chloride), Natrium phosphoricum (Sodium phosphate), Natrium sulphuricum (Sodium sulfide), Silicea terra (Silica), *Azadirachta indica, Glycyrrhiza glabra, Carduus benedictus, Carduus marianus, Juniperus communis*, and *Taraxacum officinale*. According to another embodiment, the Homeopathic Complex further comprises at least one homeopathic agent selected from the group consisting of *Centella asiatica, Curcuma longa, Eclipta alba, Emblica officinalis, Terminalia belerica* and *Terminalia chebula*. According to another embodiment, the at least one Homeopathic Complex of the delivery system comprises at least two homeopathic agents selected from the group consisting of *Antimonium crudum, Apis mellifica, Dulcamara*, Graphites, Kalium bromatum, *Ledum palustre, Rhus toxicodendron, Berberis aquifolium-Mahonia, Lappa arctium*, and *Sarsaparilla officinalis*. According to another embodiment, the Homeopathic Complex further comprises at least one homeopathic agent selected from the group consisting of *Bovista lycoperdon, Candida albicans, Echinacea augustifolia-Rudbeckia, Fumaria officinalis, Gelsemium sempervirens, Hydrocotyle asiatica, Juglans regia*, Mezereum Stramonium, Sulfur iodatum, *Taraxacum officinale, Rumex crispus*, and *Urtica urens*. According to another embodiment, the at least one Homeopathic Complex of the delivery system comprises at least two homeopathic agents selected from the group consisting of Arsenicum album (Arsenic oxide), Cactus grandiflorus-*Seleniereus spinulosus, Chelidonium majus*, Cholesteriunum, Kalium phosphoricum (Potassium phosphate), Natrium muriaticum (Sodium chloride), *Podophyllum peltatum, Sepia officinalis*, Silicea terra (Silica), and *Spigelia anthelmia*. According to another embodiment, the Homeopathic Complex further comprises at least one homeopathic agent selected from the group consisting of Calcarea sulphurica (Calcium sulfate), *Conium maculatum*, Ferrum phosphoricum (Iron phosphate), Hepar sulphuris calcareum, *Hydrastis canadensis*, Kalium carbonicum (Potassium carbonate), Kalium sulphuricum (Potassium sulfate), *Lilium tigrinum, Lycopodium clavatum*, Magnesia muriatica (Magnesium chloride), and Selenium metallicum (Selenium). According to another embodiment, the at least one Homeopathic Complex of the delivery system comprises at least two homeopathic agents selected from the group consisting of Alumina, Antimonium crudum, Fluoricum acidum (Hydrofluoric acid), Graphites, Nitricum acidum (Nitric acid), *Sepia officinalis*, Silicea terra (Silica), Sulphuricum acidum (Sulfuric acid), *Teucrium marum verum*, and *Thuja occidentalis*. According to another embodiment, the Homeopathic Complex further comprises at least one homeopathic agent selected from the group consisting of Arsenicum album (Arsenic oxide), *Bryonia alba, Candida albicans, Dioscorea villosa, Dulcamara, Echinacea purpurea*, Hepar sulphuris calcareum, Kalium carbonicum (Potassium carbonate), *Lachesis mutus, Lycopodium clavatum*, Mezereum, Phosphorus, and Zinc chloride. According to another embodiment, the at least one Homeopathic Complex of the delivery system comprises at least two homeopathic agents selected from the group consisting of *Aconitum napellus, Apis mellifica, Belladonna, Cantharis vesicatoria, Cinchona officinalis-China*, Ferrum phosphoricum (Iron phosphate), Kalium carbonicum (Potassium carbonate), Kalium muriaticum (Potassium chloride), Radium bromatum, *Sanguinaria canadensis*, and *Urtica urens*. According to another embodiment, the Homeopathic Complex further comprises at least one homeopathic agent selected from the group consisting of Aceticum acidum (Acetic acid), Arsenicum album (Arsenic oxide), *Baptisia tinctoria, Capsicum annuum*, Causticum, *Echinacea augustifolia, Euphorbium officinarum, Grindelia robusta, Hypericum perforatum*, Kalium carbonicum (Potassium carbonate), Natrium muriaticum (Sodium chloride), *Nux vomica, Rhus toxicodendron, Secale cornutum-Claviceps purpurea*, and Sulphur.

In another aspect, the present invention provides a Homeopathic Colored Pigment Product comprising (a) a coloring agent containing a plurality of particles having at least one surface and (b) a homeopathically effective amount of at least one Homeopathic Complex, wherein the at least one surface of the particles in the plurality of particles of the coloring agent comprises the at least one Homeopathic Complex and wherein the coloring agent is a cosmetically acceptable coloring agent. According to one embodiment of the Homeopathic Colored Pigment Product, the coloring agent is at least one coloring agent selected from the group consisting of mica, titanium dioxide, iron oxide, ferric ferrocyanide, ultramarine blue, clay, starch, aloe powder, corn starch, arrowroot powder, and zinc oxide. According to another embodiment, the at least one Homeopathic Complex of the Homeopathic Colored Pigment Product comprises at least two homeopathic agents selected from the group consisting of Calcarea fluorica-Fluor spar (Calcium fluoride), Calcarea phosphorica (Calcium phosphate), Calcarea sulphurica (Calcium sulfate), Ferrum phorphoricum (Iron phosphate), Kalium carbonicum (Potassium carbonate), Kalium muriaticum (Potassium chloride), Kalium phosphoricum (Potassium phosphate), Kalium sulphuricum (Potassium sulfate), Magnesia phorphoricum (Magnesium phosphate), Natrium muriaticum (Sodium chloride), Natrium phosphoricum (Sodium phosphate), Natrium sulphuricum (Sodium sulfide), Silicea terra (Silica), *Azadirachta indica, Glycyrrhiza glabra, Carduus benedictus, Carduus marianus, Juniperus communis*, and *Taraxacum officinale*. According to another embodiment, the Homeopathic Complex further comprises at least one homeopathic agent selected from the group consisting of *Centella asiatica, Curcuma longa, Eclipta alba, Emblica officinalis, Terminalia belerica* and *Terminalia chebula*. According to another embodiment, the at least one Homeopathic Complex of the Homeopathic Colored Pigment Product comprises at least two homeopathic agents selected from the group consisting of *Antimonium crudum, Apis mellifica, Dulcamara*, Graphites, Kalium bromatum, *Ledum palustre, Rhus toxicodendron, Berberis aquifolium-Mahonia, Lappa arctium*, and *Sarsaparilla officinalis*. According to another embodiment, the at least one Homeopathic Complex further comprises at least one homeopathic agent selected from the group consisting of *Bovista lycoperdon, Candida albicans, Echinacea augustifolia-Rudbeckia, Fumaria officinalis, Hydrocotyle asiatica, Juglans regia, Taraxacum officinale, Rumex crispus*, and *Urtica urens*. According to another embodiment, the at least one Homeopathic Complex of the Homeopathic Colored Pigment Product comprises at least two homeopathic agents selected from the group consisting of Arsenicum album (Arsenic oxide), Cactus grandiflorus-*Selenicereus spinulosus, Chelidonium majus*, Cholesteriunum, Kalium phosphoricum (Potassium phosphate), Natrium muriaticum (Sodium chloride), *Podophyllum peltatum, Sepia officinalis*, Silicea terra, and *Spigelia anthelmia*. According to another embodiment, the at least one Homeopathic Complex further comprises at least one homeopathic agent selected from the group consisting of Calcarea sulphurica (Calcium sulfate), *Conium maculatum*, Ferrum phosphoricum (Iron phosphate), Hepar sulphuris calcareum, *Hydrastis canadensis*, Kalium carbonicum (Potassium carbonate), Kalium sulphuricum (Potassium sulfate), *Lilium tigrinum, Lycopodium clavatum*, Magnesia muriatica (Magnesium chloride), and Selenium metallica (Selenium). According to another embodiment, the at least one Homeopathic Complex of the Homeopathic Colored Pigment Product comprises at least two homeopathic agents selected from the group consisting of Alumina, *Antimonium crudum*, Fluoricum acidum (Hydrofluoric acid), Graphites, Nitricum acidum (Nitric acid), *Sepia officinalis*, Silicea terra (Silica), Sulphuricum acidum (Sulfuric acid), *Teucrium marum verum*, and *Thuja occidentalis*. According to another embodiment, the Homeopathic Complex further comprises at least one homeopathic agent selected from the group consisting of Arsenicum album (Arsenic oxide), *Bryonia alba, Candida albicans, Dioscorea villosa, Dulcamara, Echinacea purpurea*, Hepar sulphuris calcareum, Kalium carbonicum (Potassium carbonate), *Lachesis mutus, Lycopodium clavatum*, Mezereum, Phosphorus, and Zincum metallicum (Zinc). According to another embodiment, the at least one Homeopathic Complex of the Homeopathic Colored Pigment Product comprises at least two homeopathic agents selected from the group consisting of *Aconitum napellus, Apis mellifica, Belladonna, Cantharis vesicatoria, Cinchona officinalis-China*, Ferrum phosphoricum (Iron phosphate), Kalium carbonicum (Potassium carbonate), Kalium muriaticum (Potassium chloride), Radium bromatum, *Sanguinaria canadensis*, and *Urtica urens*. According to another embodiment, the Homeopathic Complex further comprises at least one homeopathic agent selected from the group consisting of Aceticum acidum (Acetic acid), Arsenicum album (Arsenic oxide), *Baptisia tinctoria, Capsicum annuum*, Causticum, *Echinacea augustifolia, Euphorbium officinarum, Grindelia robusta, Hypericum perforatum*, Kalium carbonicum (Potassium carbonate), Natrium muriaticum (Sodium chloride), *Nux vomica, Rhus toxicodendron, Secale cornutum-Claviceps purpurea*, and Sulphur.

In another aspect, the present invention provides a method to deliver to a subject in need thereof a cosmetic formulation comprising at least one Homeopathic Complex, the method comprising the steps of: (a) obtaining a coloring agent comprising a plurality of particles having at least one surface, (b) preparing the at least one Homeopathic Complex; (c) contacting the coloring agent comprising a plurality of particles having at least one surface with the at least one Homeopathic Complex so that the at least one surface of the plurality of particles of the coloring agent comprises a homeopathically effective amount of the at least one Homeopathic Complex; (d) preparing a formulation of the coloring agent comprising a homeopathically effective amount of the at least one Homeopathic Complex; and (e) applying the formulation to the skin of the subject. According to one embodiment of the method, the coloring agent is at least one coloring agent selected from the group consisting of mica, titanium dioxide, iron oxide, ferric ferrocyanide, ultramarine blue, a clay, starch, arrowroot powder, corn starch, aloe powder and zinc oxide. According to another embodiment, the cosmetic formulation is in the form of a foundation make-up. According to another embodiment, the cosmetic formulation is in the form of a blush make-up. According to another embodiment, the cosmetic formulation is in the form of an eye shadow make-up. According to another embodiment, the cosmetic formulation is in the form of an eye liner. According to another embodiment, the cosmetic formulation is in the form of a lip liner. According to another embodiment, the cosmetic formulation is in the form of a lipstick. According to another embodiment, the cosmetic formulation is in the form of a lip gloss. According to another embodiment, the cosmetic formulation is in the form of a nail polish. According to another embodiment, the cosmetic formulation is in the form of a sunscreen. According to another embodiment, the cosmetic formulation is in the form of a face cream. According to another embodiment, the cosmetic formulation is in the form of a lotion. According to another embodiment, the cosmetic formulation is in the form of a facial serum. According to another embodiment, the cosmetic formulation is in the form of a facial scrub. According to another embodiment, the at least one Homeopathic Complex comprises at least two homeopathic agents selected from the group consisting of Calcarea fluorica-Fluor spar (Calcium fluoride), Calcarea phosphorica (Calcium phosphate), Calcarea sulphurica (Calcium sulfate), Ferrum phosphoricum (Iron phosphate), Kalium carbonicum (Potassium carbonate), Kalium muriaticum (Potassium chloride), Kalium phosphoricum (Potassium phosphate), Kalium sulphuricum (Potassium sulfate), Magnesia phorphoricum (Magnesium phosphate), Natrium muriaticum (Sodium chloride), Natrium phorphoricum (Sodium phosphate), Natrium sulphuricum (Sodium sulfide), Silicea terra (Silica), *Azadirachta indica* (Neem), *Glycyrrhiza glabra* (Licorice root), *Carduus benedictus* (Blessed Thistle), *Carduus marianus* (St. Mary's Thistle), *Juniperus communis* (Juniper Berries), and *Taraxacum officinale* (Dandilion). According to another embodiment, the Homeopathic Complex further comprises at least one homeopathic agent selected from the group consisting of *Centella asiatica* (Gota Kola), *Curcuma longa* (Turmeric), *Eclipta alba* (Bhringaraj), *Emblica officinalis* (Indian Gosseberry), *Terminalia belerica* and *Terminalia chebula*. According to another embodiment, the at least one Homeopathic Complex comprises at least two homeopathic agents selected from the group consisting of Antimonium crudum (Black Sulphide of Antimony), *Apis mellifica* (The Honey Bee), *Dulcamara* (Bitter sweet), Graphites, Kalium bromatum, *Ledum palustre, Rhus toxicodendron, Berberis aquifolium-Mahonia, Lappa arctium*, and *Sarsaparilla officinalis*. According to another embodiment, the at least one Homeopathic Complex further comprises at least one homeopathic agent selected from the group consisting of *Bovista lycoperdon, Candida albicans, Echinacea augustifolia-Rudbeckia, Fumaria officinalis, Hydrocotyle asiatica, Juglans regia, Taraxacum officinale, Rumex crispus*, and *Urtica urens*. According to another embodiment, the at least one Homeopathic Complex comprises at least two homeopathic agents selected from the group consisting of Arsenicum album (Arsenic oxide), Cactus grandiflorus-*Selenicereus spinulosus, Chelidonium majus*, Cholesteriunum, Kalium phosphoricum (Potassium phosphate), Natrium muriaticum (Sodium chloride), *Podophyllum peltatum, Sepia officinalis*, Silicea terra (Silica), and *Spigelia anthelmia*. According to another embodiment, the at least one Homeopathic Complex further comprises at least one homeopathic agent selected from the group consisting of Calcarea sulphurica (Calcium sulfate), *Conium maculatum*, Ferrum phosphoricum (Iron phosphate), Hepar sulphuris calcareum, *Hydrastis canadensis*, Kalium carbonicum (Potassium carbonate), Kalium sulphuricum (Potassium sulfate), *Lilium tigrinum, Lycopodium clavatum*, Magnesia muriatica (Magnesium chloride), and Selenium metallicum (Selenium). According to another embodiment, the at least one Homeopathic Complex comprises at least two homeopathic agents selected from the group consisting of Alumina, Antimonium crudum, Fluoricum acidum (Hydrofluoric acid), Graphites, Nitricum acidum (Nitric acid), *Sepia officinalis*, Silicea terra (Silica), Sulphuricum acidum (Sulfuric acid), *Teucrium marum verum*, and *Thuja occidentalis*. According to another embodiment, the at least one Homeopathic Complex further comprises at least one homeopathic agent selected from the group consisting of Arsenicum album (Arsenic oxide), *Bryonia alba, Candida albicans, Dioscorea villosa, Dulcamara, Echinacea purpurea*, Hepar sulphuris calcareum, Kalium carbonicum (Potassium carbonate), *Lachesis mutus, Lycopodium clavatum*, Mezereum, Phosphorus, and Zincum metallicum (Zinc). According to another embodiment, the at least one Homeopathic Complex comprises at least two homeopathic agents selected from the group consisting of *Aconitum napellus, Apis mellifica, Belladonna, Cantharis vesicatoria, Cinchona officinalis-China*, Ferrum phosphoricum (Iron phosphate), Kalium carbonicum (Potassium carbonate), Kalium muriaticum (Potassium chloride), Radium bromatum, *Sanguinaria canadensis*, and *Urtica urens*. According to another embodiment, the at least one Homeopathic Complex further comprises at least one homeopathic agent selected from the group consisting of Aceticum acidum (Acetic acid), Arsenicum album (Arsenic oxide), *Baptisia tinctoria, Capsicum annuum*, Causticum, *Claviceps purpurea, Echinacea augustifolia, Euphorbium officinarum, Grindelia robusta, Hypericum perforatum*, Kalium carbonicum (Potassium carbonate), Natrium muriaticum (Sodium chloride), *Nux vomica, Rhus toxicodendron, Secale cornutum-Claviceps purpurea*, and Sulphur.

DETAILED DESCRIPTION OF THE INVENTION

In one aspect, the present invention provides a delivery system to deliver topically to a subject in need thereof a homeopathically effective amount of at least one Homeopathic Complex. The delivery system comprises (a) the homeopathically effective amount of the at least one Homeopathic Complex; and (b) a coloring agent comprising a plurality of particles having at least one surface, wherein the Homeopathic Complex contacts at least one surface of the plurality of particles of the coloring agent.

In another aspect of the present invention, a Homeopathic Colored Pigment Product comprises (a) a coloring agent comprising a plurality of particles having at least one surface; and (b) a homeopathically effective amount of at least one Homeopathic Complex, wherein at least one surface of the particles in the plurality of particles of the coloring agent comprises the at least one Homeopathic Complex, and wherein the coloring agent is a cosmetically acceptable coloring agent.

In another aspect of the present invention, a method to deliver to a subject in need thereof a cosmetic formulation comprising at least one Homeopathic Complex comprises the steps of: (a) obtaining a coloring agent comprising a plurality of particles having at least one surface, (b) preparing the at least one Homeopathic Complex; (c) contacting the coloring agent comprising a plurality of particles having at least one surface with the at least one Homeopathic Complex so that the at least one surface of the particles in the plurality of particles of the coloring agent comprises a homeopathically effective amount of the at least one Homeopathic Complex; (d) preparing a formulation of the coloring agent comprising a homeopathically effective amount of the at least one Homeopathic Complex; and (e) applying the formulation to the skin of the subject.

The term "active" as used herein refers to the ingredient, component or constituent of the compositions of the present invention responsible for the intended therapeutic effect.

The term "Homeopathic Complex" as used herein refers to two or more homeopathic agents.

Agents used in homeopathy ("Homeopathic agents") are derived from natural, biological and mineral sources and are selected from a large list of possible agents. Such agents are set forth in various compendia of homeopathic agents used in medicine, which include their origins, preparation, uses, and effects, known as "Materia Medica" and are generally included in the Homeopathic Pharmacopoeia of the United States ("HPUS"). See also Frans Vermeulen, Concordant Materia Medica, Emryss Publishers, Millenium edition November 2000; Margarethe Harrms, Homoopathische Mittel und ihre Wirkungen Materia Medica und Repertorium), Verlag Grundlagen und Praxis (publisher), Leer (1973); Drs Léon Vannier & Jean Poirier; Précis de Matiére Medicale Homoepathique 8th Edition Revue Corrigee et Augmentée; 8, Place de L'Odéon, Paris (11968); Timothy F. Allen; Ed., The Encyclopedia of Pure Materia Medica, B Jain Publishers; 55/I Arjua Nagar, New Delhi (1976).

A useful source book on the subject is Boericke, William, New Manual of Homeopathic Materia Medica & Repertory, Ninth Ed., New Delhi: B. Jain (P.) Ltd., 2005. The appropriate methods of preparation as well as formulations appropriate for human use of each agent is collected in HPUS. The present edition of HPUS, the Homeopathic Pharmacopoeia of the United States Revision Service, Pharmacopoeia Convention of the Amerimay Institute of Homeopathy, 1988 (HPRS) is the official compendium of homeopathic agents recognized by the United States Food and Drug Administration (FDA) under the Federal Food, Drug, and Cosmetic Act. The contents of each of these references that relate to the present invention are incorporated by reference herein in their entirety.

Table 1 sets out a partial list of commonly used homeopathic agents useful in the present invention. Common names for many of these agents are indicated in parentheses and may be used interchangeably herein with the Latin names.

TABLE 1

Homeopathic Agents

| | | |
|---|---|---|
| *Abrotanum* (Southernwood, Old Man; Lady's Love) | Aceticum acidum (Glacial Acetic Acid) | *Aconitum napellus* (Aconite; Friar's Cap; Helmet Flower; Monkshood; Wolfsbane) |
| *Aesculus hippocastanum* (Horse Chestnut; Common Horse Chestnut) | Aethiops mineralis (Sulphur and Quicksilver, or Black Sulphide Mercury) | *Agaricus muscarius* - *Amanita* (Toad Stool-Bug Agaric) |
| *Alnus rubra* (Red Alder) | *Aloe socotrina* (*Aloes*; *Curacao Aloe*; *Cape aloe*, *Socotrine Aloes*) | Alumina (Oxide of Aluminium-Arigilla, Aluminum Oxide; Alumina, Argilla) |
| Ammonium benzoicum (Ammonium, Benzoate of Ammonium) | *Anacardium orientale* (Marking Nut) | Anthrakokali (Anthracite Coal Dissolved in Boiling Caustic Potash) |
| Antimonium crudum (Antimony Trisulfide, Black Sulphide of Antimony)) | Antimonium sulphuratum auratum (Golden Sulphuret of Antimony) | Antimonium tartaricum (Tartar Emetic, Tartrate of Antimony and Potash) |
| *Apis mellifica* (The Honey-Bee, Whole Honey Bee) | *Arbutus andrachne* (Strawberry Tree) | Argentum nitricum (Nitrate of Silver) |
| *Arnica montana* (Leopard's Bane) | Arsenicum album (Arsenious Acid-Arsenic Trioxide) | Arsenicum bromatum (Bromide of Arsenic) |
| Arsenicum iodatum (Iodide of Arsenic) | Arsenicum sulfuratum flavum - Arsenic trisulph | *Arundo mauritanica* (Reed) |
| *Asimina triloba* (American Papaw-Carica Papaya) | *Asterias rubens* (Red Starfish) | *Azadirachta indica* (Margosa; Nim; Neem, Melia azadirchta) |
| *Badiaga* (Fresh-water Sponge) | *Baptisia tinctoria* (Wild Indigo; Horsefly Weed; Indigo Broom; Ratlike Bush; Yellow Broom) | Baryta carbonica (Barium Carbonate, Carbonate of Baryta) |
| *Belladonna* (Deadly Nightshade; Banewort; Death's Herb; Dwale; Poison Black Cherry) | *Bellis perennis* (Daisy) | *Berberis aquifolium* - *Mahonia* (Mountain Grape; Oregon Grape; Holly-leaved Barberry) |
| *Berberis vulgaris* (Barberry, Jaundice Berry; Pepperidge Bush; Sour-spine) | Borax veneta (Borate of Sodium, Sodium Borate; Sodium Biborate; Sodium Tetraborate) | *Bovista lycoperdon* (Puff Ball; Warted Puff Ball) |
| *Bryonia alba* (White Bryony; Black-berried Bryony, Wild Hops) | *Cactus grandiflorus* - *Selenicereus spinulosus* (Night-blooming *Cereus*; Moon *Cereus*) | Calcarea carbonica-ostrearum (Impure Calcium Carbonate; Oyster Shells, Carbonate of Lime) |
| Calcarea fluorica - Fluor spar. (Calcium Fluoride, Fluoride of Lime) | Calcarea iodata (Iodide of Lime) | Calcarea phosphorica (Phosphate of Lime) |
| Calcarea silicata (Silicate of Lime) | Calcarea sulphurica (Sulphate of Lime-Plaster of Paris) | *Calendula officinalis* (Marigold) |
| *Camphora officinalis* ( | *Camphora officinalis* (Camphor) | *Candida albicans* (Yeast) |
| *Candida albicans* (Yeast) | *Cantharis vesicatoria* (Spanish Fly; Blistering Fly; Blistering Beetle) | *Capsicum annuum* (Cayenne Pepper; Red Pepper; Paprika) |
| Carbo animalis (Animal Charcoal) | Carbo vegetabilis (Vegetable charcoal) | Carbo vegetabilis (Vegitable Charcoal) |
| Carbolicum acidum (Phenol-Carbolic Acid) | *Carduus benedictus* (Blessed Thistle; Holy Thistle) | *Carduus marianus* (St. Mary's Thistle; Milk thistle) |
| *Castor equi* (Rudimentary Thumb-nail of the Horse) | Causticum (Hahnemann's Tincture acris sine Kali) | *Centella asiatica* (Gotu Kola) |
| *Chamomilla* (German Chamomile) | *Chelidonium majus* (Greater Celandine; Swallow-wort; Tetterwort; Celandine) | Cholesterinum (Cholesterine-The proximate principle. Furnished by the epithelium lining of the gall bladder and larger ducts, Cholesterol) |
| *Chrysarobinum* (Goa Powder-Andira araroba) | *Cicuta virosa* (Water Hemlock) | *Cimicifuga racemosa* (Actaea Racemose) (Macrotys) (Black Snake-root) |
| *Cinchona officinalis* - China (Cinchona; Calisaya Bark; Peruvian Bark; Jesuit's Bark) | *Clematis erecta* (Virgin's Bower) | Cobaltum metallicum (The Metal Cobalt) |
| *Coffea cruda* (Unroasted Coffee) | *Comocladia dentate* (Guao) | *Conium maculatum* (Poison Hemlock; Herb-bennet; Poison Parsley; Spotted Hemlock) |
| *Crataegus oxyacantha* (Hawthorn Berries) | *Crotalus horridus* (Rattlesnake) | *Croton tiglium* (Croton-oil Seed) |
| *Cunderango* (Condor Plant) | *Curcuma longa* (Turmeric) | *Dioscorea villosa* (Wild Yam; Colic Root; Rheumatism Root) |
| *Dulcamara* (Bitter-sweet, Scarlet Berry; Violet Bloom; Woody Nightshade; Blue Bindweed; Fellenwort) | *Echinacea augustifolia* - Rudbeckia (Coneflower; Black Sampson; Pale Purple Cone-flower; *Echinacea*) | *Echinacea purpurea* (Black Sampson; Eastern Purple Cone-flower) |
| *Eclipta alba* (Bhringaraj) | *Elaps corallinus* (Coral-snake) | *Emblica officinalis* (Indian Gooseberry) |
| *Eugenia jambos* - *Jambosa vulgaris* (Rose-apple) | *Euphorbium officinarum* (Spurge-The Resinous Juice of *Euphorbia Resinifera*, Gum *Euphorbium*, Spurge) | *Euphrasia officinalis* (Eyebright) |
| Ferrum phosphoricum (Phosphate of Iron) | Ferrum phosphoricum (Phosphate of Iron, Iron Phosphate) | Fluoricum acidum (Hydrofluoric Acid; Hydrogen Fluoride Solution)) |
| *Formica rufa* (Myrmexine) (Crushed Live Ants) | *Fraxinus americana* (White Ash) | *Fuligo* ligni (Soot) |
| *Fumaria officinalis* (Beggary; Common Fumitory; Earth Smoke) | *Gelsemium sempervirens* (Yellow Jasmine) | *Ginseng quinque folium* (*Aralia quinquefolia*-Wild *Ginseng-Panax*) |
| *Glycyrrhiza glabra* (Licorice Root) | Granatum (Pomegranate) | Graphites (Plumbago; Black Lead-Plumbago) |
| *Grindelia robusta* (Rosin-wood) | *Hamamelis virginiana* (Witch-hazel; Winter Bloom; Snapping Hazel; Striped | *Helliborus niger* (Snow-rose) |

TABLE 1-continued

Homeopathic Agents

| | Alder) | |
|---|---|---|
| Hepar sulfuris calcareum (Impure Calcium Sulfide; Liver of Sulfur, Hahnemann's Calcium Sulphine) | *Hippozaeninum* (Gladerine-mallein-Farcine) | *Histaminum hydrochloricum* |
| *Hydrastis canadensis* (Golden Seal; Orange Root; Yellow Root; Indian Turmeric) | *Hydrocotyle asiatica* (Indian Pennywort; Water Pennywort) | Hydrocyanicum acidum (Prussic acid) |
| *Hypericum perforatum* (St. John's-wort) | *Ignatia Amara* (St. Ignatius Bean) | Iodium (Iodine) |
| *Iris versicolor* (Blue Flag; Wild *Iris*; Flag Lily) | *Juglans cinerea* (Butternut) | *Juglans regia* (Walnut) |
| *Juniperus communis* (Common Juniper, Juniper Berries) | Kalium arsenicosum (Fowler's Solution) | Kalium bichromicum (Bichromate of Potash) |
| Kalium bromatum (Bromide of Potash, Potassium Bromide) | Kalium carbonicum (Carbonate of Potassiuom, Potassium Carbonate, Anhydrous) | Kalium hydriodicum (Iodide of Potassium) |
| Kalium phosphoricum (Phosphate of Potassium) | Kalium sulphuricum (Potassium Sulphate) | *Kreosotum* (Beechwood Kreosote) |
| *Lachesis mutus* (Bushmaster, Surucucu) | *Lappa arctium* (Burdick, Great Burdock) | *Ledum palustre* (Wild Rosemary; Marsh Cistus; Marsh Tea; Silesian Rosemary) |
| *Lilium tigrinum* (Tiger Lily; Spotted Lily) | Lithium carbonicum (Carbonate of Lithium) | *Lycopodium clavatum* (Club Moss; Running Pine; Vegetable Sulfur) |
| *Lycopus virginicus* (Bugle-weed; Sweet Bugle; Water Bugle) | Magnesia carbonica (Carbonate of Magnesia, Magnesium Carbonate Hydroxide; Basic Magnesium Carbonate) | Magnesia muriatica (Muriate of Magnesia) |
| Magnesia muriatica (Muriate of Magnesia, Magnesium Chloride Hexahydrate) | Magnesia phosphorica (Phosphate of Magnesia) | *Magnolia grandiflora* (Magnolia) |
| *Mancinella* (Hippomane-Manganeel Apple) | Manganum aceticum (Manganese Acetate) | *Medusa* (Jelly-fish) |
| Mercurius corrosivus (Corrosive Sublimate | Mercurius cyanatus (Cyanide of Mercury) | Mercurius dulcis (Mild Mercury Chloride, Calomel) |
| Mercurius iodatus ruber (Bin-iodide of Mercury) | Mercurius solubilis - Hydrargyrum (Quicksilver) | *Mezereum* (Spurge Olive, Mezeneum; Mezereon; Olive Spurge; Swarf Bay; Daphne Mezereum L.) |
| *Morphinum* (An Alkaloid of Opium) | *Murex purpurea* (Purple Fish) | Muriaticum acidum (Muriatic Acid) |
| Natrium arsenicosum (Arseniate of Sodium, Sodium Arsenate) | Natrium carbonicum (Carbonate of Sodium, Sodium Carbonate) | Natrium hypochlorosum (Chlorate of Sodium-Labarraque's Solution) |
| Natrium muriaticum (Chloride of Sodium, Sodium Chloride) | Natrium phosphoricum (Phosphate of Sodium) | Natrium Sulphuricum (Sulphate of Sodium-Glauber's Salt) |
| Nitricum acidum (Nitric Acid) | *Nux moschata* (Nutmeg) | *Nux vomica* (Poison-nut; Quaker Buttons) |
| Oleander - Nerium odorum (Rose-laurel) | *Oleum jecoris aselli* (Cod Liver Oil) | *Oophorinum* (Ovarian Extract) |
| Opium - *Papaver somniferum* (Dried Latex of the Poppy) | Osmium metallicum (The Element) | *Petroleum* (Crude Rock-oil) |
| Phosphoricum acidum (Phosphoric Acid) | Phosphorus (Phosphorus) | *Phytolacca decandra* (Poke-root) |
| *Piper methysticum* (Kava-kava) | Plumbum metallicum (Lead) | *Podophyllum peltatum* (May-apple; Amerimay Mandrake) |
| *Polygonum punctatum* (Hydropiper) (Smartweed) | *Primula veris* (Cowship) | Psorinum (Scabies Vesicle) |
| *Ptelea trifoliate* (Water-Ash) | *Pulex irritans* (Common Flea) | *Pulsatilla pratensis* (Wind Flower) |
| Radium bromatum (Radium Bromide) | *Ranunculus bulbosus* (Buttercup) | *Raphanus sativus* (Black Garden Radish) |
| *Rhus toxicodendron* (Poison-ivy) | *Rhus venenata* (Poison-elder) | *Rumex crispus* (Sour Dock, Yellow Dock, Curly Dock) |
| *Ruta graveolens* (Rue-bitterwort) | *Sabadilla* (Cevadilla Seed. *Asagrae Officialis*) | *Sabal serrulata* (Saw Palmetto) |
| *Sabina* (Savine) | Sanguinaria canadensis (Blood Root) | Sanicula aqua (the Water of Sanicula Springs, Ottawa, Ill) |
| *Sarsaparilla officinalis* (Smilax) | Secale cornutum - *Claviceps purpurea* (Ergot) | Selenium metallicum (the Element Selenium) |
| *Sepia* officinalis (Inky Juice of Cuttlefish, the Inky Juice of Common or European Cuttlefish) | Silicea terra (Silica. Pure Flint) | Skookum-chuck (Strong Medicinal Water. Salts from Water of Medical Lake near Spokane, WA) |
| *Solidago virgaurea* (Golden-rod) | *Spigelia anthelmia* (Pinkroot) | *Staphysagria* (Stavesacre) |
| *Stramonium* (Thorn-apple) | Sulfur (Sublimated Sulphur) | Sulfur iodatum (Iodide of Sulphur) |
| Sulphuricum acidum (Sulfuric Acid) | Sulphurosum acidum (Sulphurous Acid) | *Sumbullus moschatus - Ferula sumbul* (Musk-root) |
| *Tabacum* (Tobacco) | *Taraxacum officinale* (Dandelion) | Tellurium metallicum (The Metal Telluricum) |
| *Terminalia belerica* (Bahada) | *Terminalia chebula* (Haritaki) | *Teucrium marum verum* (Cat-thyme) |
| Thallium metallicum (The Metal Thallium) | *Thuja occidentalis* (Arbor vitae) | *Tuberculinum bovinum* kent (A Nucleo-Protein, a Nosode from Tubercular Abcess) |
| *Urtica urens* (Stinging-nettle) | *Ustilago maydis* (Corn-smut) | *Veratrum album* (White Hellebore) |
| *Verbascum thapsus* (Mullein) | *Vespa crabro* (Live Wasp) | *Vinca minor* (Lesser Periwinkle) |
| *Viola tricolor* (Pansy) | *Vipera berus* (The German Viper) | X ray (Vial Containing Alcohol Exposed |

TABLE 1-continued

Homeopathic Agents

| | | |
|---|---|---|
| *Xerophyllum* (Tamalpais Lily. Basket grass Flower) | Zincum metallicum (Zinc) | to X-ray) |

The twelve Cell Salts and some representative indications or deficiency symptoms, as described in a treatise by Lennon, Nigey and Lionel Rolfe (Homeopathic Cell Salt Remedies, Healing With Nature's Twelve Mineral Compounds, Garden City Park: Square One, 2004), are shown in table 2. Common names for the Cell Salts are indicated in parentheses and are used interchangeably herein with the Latin names.

TABLE 2

Twelve Cell Salts and Corresponding Indication/Deficiency Symptoms

| Agent | Indication/deficiency symptoms |
|---|---|
| Calcarea fluorica - Fluor spar. (Fluoride of Lime, Calcium fluoride) | Treats problems with the surface of bones and skin. A safer source of fluoride than supplemental fluoride. Deficiency symptoms include poor dental enamel, spider and varicose veins. |
| Calcarea phosphorica (Phosphate of Lime, Calcium Phosphate) | Promotes growth and health of the bones. Deficiency symptoms include aching pains, growing pains, bone ailments |
| Calcarea sulphurica (Sulphate of Lime, Calcium sulfate) | Deficiency symptoms include acne and other skin problems, slow healing wounds, abscesses, swollen glands, negativity, apathy. |
| Kalium muriaticum (Chloride of Potassium, Potassium chloride) | Deficiency symptoms include colds, sinus inflammation, arthritis inflammation, lack of energy and interest |
| Kalium phosphoricum (Phosphate of Potassium, Potassium phosphate) | Deficiency symptoms include anxiety, irritability, poor memory and physical fatigue. |
| Kalium sulphuricum (Potassium Sulfate) | Corrects the functioning of oils in the body. Deficiency symptoms manifest as dryness and in the later stages of inflammation including acne and intestinal disorders. Mental symptoms include worry and lack of judgment. |
| Natrium muriaticum (Chloride of Sodium, Sodium Chloride) | Helps with edema (swelling), headache, weakness in the sun or heat, chronic sinus conditions. |
| Natrium phosphoricum (Phosphate of Sodium, Sodium Phosphate) | Commonly used for complaints of the digestive system. Take right before meals for improved digestion. Deficiency symptoms include acidity and indigestion. |
| Natrium sulphuricum (Sulphate of Sodium-Glauber's Salt, Sodium Sulfate) | Commonly used to strengthen pancreatic functioning. |
| Ferrum phosphoricum (Phosphatge of Iron, Ferrum Phosphate) | Known as the "Oxygenating cell salt", commonly used to treat physical fatigue. Useful for inflammation, fever and infection. |
| Magnesia phosphorica (Phosphate of Magnesia, Magnesium Phosphate) | Found inside the cells of muscles and nerves. Deficiency symptoms include muscle pain, muscle fatigue and muscle spasms. |
| Silicea terra (Silica, Pure Flint) | The hair and skin remedy. Deficiency includes excess perspiration, unhealthy skin, brittle nails and hair. |

The guiding principle of homeopathy is that the potency of a remedy may be enhanced and the side-effects diminished by dilution, in a procedure known as "attenuation". As used herein, the terms "triturating", "trituration", or "triturate" are used to mean to reduce to fine particles or powder by rubbing, grinding, or otherwise pulverizing.

The proportion of measure and weight employed in the preparation of aqueous solutions, alcoholic solutions, liquid attenuations, and triturations varies according to the solubility and physical, chemical, biological or botanical characteristics of the original substance.

The first liquid attenuation or first trituration usually represents one-tenth (0.1) unit of the original substance, but may vary according to the specifications of the monograph of an individual drug. Attenuation most commonly is performed by decimal or centesimal progression as directed under the following classes. Liquids are progressively diluted with water and alcohol and shaken by hard strikes against an elastic body in a practice known as succussion. Insoluble solids, such as quartz and oyster shell, are diluted by grinding with lactose, in a process known as trituration. Dilutions are generally made serially using a 1 part in 10 or decentesimal scale (X potency) or 1 part in 100 or centesimal scale (C potency). Higher 'potencies' up to 1 part in 50,000 or Quintamillesimal (LM or Q potencies) though rare, are used to treat long standing, chronic symptoms and are more non-specific in nature in that they treat more general areas of the body.

For example, a decimal progression takes 1 part of a medicinal substance (dry or tincture) mixed with 9 parts diluent, which then is succussed, to yield the 1X potency. Taking 1 part of the 1X potency and mixing it with 9 parts diluent, which then is succussed, yields the 2X potency. This is continued until the desired potency is reached.

Alternatively, centesimal progression takes 1 part medicinal substance (dry or tincture) mixed with 99 parts diluent, which then is succussed, to yield the 1C potency. Taking 1 part of that potency mixed with 99 parts diluent, which then is succussed, yields the 2C potency. This is continued until the desired potency is reached.

The term "potency" refers to the strength of a homeopathic remedy, or the relative amount of a substance required to produce the desired response. It is determined by how many time the remedy has been succussed (or triturated) and diluted during preparation. The terms "potenization" and "potenization process" therefore are used interchangeably to refer to the process of dilution plus succussion or the process of dilution plus triturition. Skilled artisans have understood dilution (also known as attenuation) and dynamization (also known as succussion) to have resulted in potentization. Today however some also use the terms potentization and attenuation interchangeably.

Homeopathic potencies are designated by a combination of a number and a letter, for example, 10X or 30C. The number indicates the number of dilutions the original substance has undergone within a series to prepare that particular remedy. The letter refers to the proportions used in each of the dilutions in that series. While dilutions greater than 23X are unlikely to contain the original molecules, it is widely recognized and accepted in the art that the water retains "essential properties" of the homeopathic substances with which it has come in contact through means of succussion (or trituration), thus allowing homeopathic medicine to heal without producing side effects.

Most medicines used in homeopathic practice may be prepared in the form of tinctures. The terms "tincture" or "tinctures" as used herein refer to solutions prepared from an original element selected from a variety of zoological or botanical substances in alcohol of various strengths. A "mother tincture", or primary dilution, is a solution of a botanical substance and alcohol made according to standards set by the Homeopathic Pharmacopoeia of the United States (HPUS). The potency of a mother tincture depends on the properties of the original substance, also referred to herein as the original element. All higher dilutions are derived from the mother tincture. Tinctures require storage in air tight, light-resistant containers, away from direct sunlight and excessive heat.

HPUS is known to those skilled in the art and contains the precise directions and proportions for preparing attenuations and triturations of known homeopathic agents, including specifically methods for liquid attenuations of soluble substances, tinctures of biological substances, tinctures of zoological substances, triturations of solid substances, triturations of insoluble liquid substances, conversion of triturations of insoluble basic substances into liquid attenuations, attenuations of pathological organs or tissues, causative agents, excretions and secretions, attenuations of antigens, attenuations of botanical, zoological or chemical substances which have been ingested or absorbed by the body, attenuations of organs, tissues and metabolic factors and tinctures of botanical substances.

HPUS also contains monographs for each known homeopathic agent which includes the appropriate classification of the agent to determine the proper method of attenuation or trituration, together with the required degree of attenuation for medical use in humans. Mother tinctures of various homeopathic agents as well as homeopathic agents prepared in various triturations and attenuations, such as 10X, are commercially, available, for example, from Newton Laboratories, 2360 Rockaway Industrial Blvd. Conyers, Ga. 30012.

The absorption of homeopathic agents applied topically is limited by the composition and action of the human skin. Human skin is responsible, inter alia, for protection of the body, regulation of body temperature, sensory reception, synthesis of vitamins and hormones, water balance and absorption of substances. It is a formidable barrier to the passage of most substances. Skin consists of two main parts: an epithelium, the epidermis, lying outermost, and beneath this a layer of connective tissue, which includes the tough collagen-rich dermis and the underlying fatty subcutaneous layer or hypodermis.

The defining component of the skin is the epidermis, which is a multilayered ("stratified") epithelium composed largely of keratinocytes that synthesize keratins, which give the epidermis its toughness. The waterproof barrier is formed by epidermal cells. The outer, horny layer of the epidermis is the stratum corneum, which consists of several layers of flat keratinized normucleated cells. The cell envelopes of the cells in the stratum corneum tend to be mainly polar lipids, such as ceramides, sterols, and fatty acids, while the cytoplasm of stratum corneum cells remains polar and aqueous. Despite the close packing of the cells, about 15% of the stratum corneum is intercellular and, generally lipid-based. The lipid-rich intercellular space in the stratum corneum comprises lamellar matrices with alternating hydrophilic layers and lipophilic bilayers formed during the process of keratinization.

The dermis comprises a fibrous protein matrix embedded in an amorphous, colloidal, ground substance. It supports and interacts with the epidermis, facilitating its conformation to underlying muscles and bones. Blood vessels, lymphatics, and nerves are found within the dermis.

As used herein, the term "topical" refers to administration of an inventive composition at, or immediately beneath, the point of application. The phrase "topically applying" describes application onto one or more surfaces(s), including epithelial surfaces. Although topical administration, in contrast to transdermal administration, generally provides a local rather than a systemic effect, as used herein, unless otherwise stated or implied, the terms topical administration and transdermal administration are used interchangeably.

Substances are applied to the skin to elicit one or more of four general effects: an effect on the skin surface, an effect within the stratum corneum; an effect requiring penetration into the epidermis and dermis; or a systemic effect resulting from delivery of sufficient amounts of a given substance through the epidermis and the dermis to the vasculature to produce therapeutic systemic concentrations. One example of an effect on the skin surface is formation of a film. Film formation may be protective (e.g., sunscreen) and/or occlusive (e.g., to provide a moisturizing effect by diminishing loss of moisture from the skin surface). One example of an effect within the stratum corneum is skin moisturization; which may involve the hydration of dry outer cells by surface films or the intercalation of water in the lipid-rich intercellular laminae; the stratum corneum also may serve as a reservoir phase or depot wherein topically applied substances accumulate due to partitioning into, or binding with, skin components.

It generally is recognized that short-term penetration occurs through the hair follicles and the sebaceous apparatus of the skin, while long term penetration occurs across cells. Penetration of a substance into the viable epidermis and dermis may be difficult to achieve, but once it has occurred, the continued diffusion of the substance into the dermis is likely to result in its transfer into the microcirculation of the dermis and then into the general circulation. It is possible, however, to formulate delivery systems that provide substantial localized delivery.

"Percutaneous absorption" is the absorption of substances from outside the skin to positions beneath the skin, including into the blood stream. The epidermis of human skin is highly relevant to absorption rates. Passage through the stratum corneum marks the rate-limiting step for percutaneous absorption. The major steps involved in percutaneous absorption of, for example, a drug include the establishment of a concentration gradient, which provides a driving force for drug movement across the skin, the release of drug from the vehicle into the skin-partition coefficient and drug diffusion across the layers of the skin-diffusion coefficient. The relationship of these factors to one another is summarized by the following equation:

$$J=Cveh \times Km \cdot D/x \qquad \text{[Formula 1]}$$

where J=rate of absorption; Cveh=concentration of drug in vehicle; Km=partition coefficient; and D=diffusion coefficient.

There are many factors that affect the rate of percutaneous absorption of a substance. Primarily they are as follows: (i) Concentration. The more concentrated the substance, the greater the absorption rate. (ii) Size of skin surface area. The wider the contact area of the skin to which the substance is applied, the greater the absorption rate. (iii) Anatomical site of application. Skin varies in thickness in different areas of the body. A thicker and more intact stratum corneum decreases the rate of absorbency of a substance. The stratum corneum of the facial area is much thinner than, for example, the skin of the palms of the hands. The facial skin's construction and the thinness of the stratum corneum provide an area of the body that is optimized for percutaneous absorption to allow delivery of active agents both locally and systemically through the body. (iv) Hydration. Hydration (meaning increasing the water content of the skin) causes the stratum corneum to swell which increases permeability. (v) Skin temperature. Increased skin temperature increases permeability. (vi) Composition. The composition of the compound and of the vehicle also determines the absorbency of a substance. Most substances applied topically are incorporated into bases or vehicles. The vehicle chosen for a topical application will greatly influence absorption, and may itself have a beneficial effect on the skin. Ideally, a vehicle has use in the present invention if it is easy to apply and remove, nonirritating, and cosmetically pleasing. Factors that determine the choice of vehicle and the transfer rate across the skin are the substance's partition coefficient, molecular weight and water solubility. The protein portion of the stratum corneum is most permeable to water soluble substances and the lipid portion of the stratum corneum is most permeable to lipid soluble substances. It follows that substances having both lipid and aqueous solubility may traverse the stratum corneum more readily. See Dermal Exposure Assessment: Principles and Applications, EPA/600/8-91/011b, January 1992, Interim Report—Exposure Assessment Group, Office of Health and Environmental Assessment, U.S. Environmental Protection Agency, Washington, D.C. 20460.

The dry Homeopathic Colored Pigment Products of the present invention do not traverse the stratum corneum on their own. Instead, they depend on the water and oil content of the skin to facilitate their delivery.

The term "color" as used herein refers to the quality of an object or substance with respect to light reflected or absorbed by the object or substance. The three characteristics of color are hue, intensity, and value. "Hue" refers to a gradation, tint, or variety of a color. "Intensity", "chroma", and "saturation" are used interchangeably to refer to the strength or sharpness of a color. A color is full in intensity only when pure and unmixed. "Value" refers to a degree of lightness or darkness in a color.

The present invention recognizes that "coloring agents", i.e., substances used to provide color, translucense, and/or opaqueness, also are capable of delivering homeopathic dilutions topically. A coloring agent according to the present invention may be of mineral, plant, animal or synthetic origin. FDA approved coloring agents may be found in volume 21 of the Code of Federal Regulations, and on the FDA website at www.efsan.fda.gov/~dms/opa-col2.html#table3A (visited Mar. 31, 2007), both of which are incorporated by reference. Examples of coloring agents include, but are not limited to, Annatto, Caramel, Carmine, Beta carotene, Bismuth citrate, Clay, Disodium EDTA-copper, Potassium sodium copper chlorophyllin (Chlorophyllin copper complex), Dihydroxyacetone, Bismuth oxychloride, Guaiazulene, Henna, Iron oxides, Ferric ammonium ferrocyanide, Ferric ferrocyanide, Chromium hydroxide green, Chromium oxide green, Guanine, Kaolin Clay, Lead acetate, Pyrophyllite, Mica, Serecite, Silver, Titanium dioxide, Aloe powder, Aluminum powder, Arrowroot powder, Bronze powder, Copper powder, Corn starch, Ultramarines, Manganese violet, Zinc Oxide, and Luminescent zinc sulfide, Talc, starches, natural Dyes, such as Walnut extract, Rhubarb extract, Cinchona extract, Henna, Woad, Weld, Dyer's Greenweed, Buckthorn berries, Safflower, Saffron, Madder, Brazilwood (Sappanwood), Indigo, Alkanet, Logwood, Various mushrooms, Lichens, Murex purple, Kermes, Lac and Cochineal, Anthocyanins, Betacyanins, Caramel, Carmine, Carotenoids, Chlorophylls, Riboflavin, Turmeric, vegetable dyes, animal extracts, plant extract, and other mineral and/or synthetic coloring agents. The quantities of coloring agents will vary depending on the shade and tint desired in the final color pigment product. Any coloring agent that contains a plurality of particles having at least one surface that is suitable for use in cosmetics, i.e., on living skin, may be used in the present invention.

A Homeopathic Colored Pigment Product according to the present invention comprises a coloring agent comprising particles having at least one surface. The term "particle" is used herein to refer to a very small portion, piece, or fragment of a solid material. According to the present invention, at least one Homeopathic Complex is applied to, or contacts, at least one surface of the particles of the coloring agent. As used herein, the terms "contact" and "applied to" are used interchangeably to refer to the state or condition of touching or of being in immediate proximity.

Particle size and rheology (meaning flow characteristics) often are key indicators of a cosmetic product's final performance. Liposomes often are used when formulating a moisturizing product, because moisturizing products need to rapidly absorb into the skin. Such particles generally measure less than about 200 nm.

When formulating a lipstick, the color density of lipstick generally is influenced by the type and particle size distribution of the coloring agents used. The degree of gloss or frosting is achieved by varying the particle size distribution—greater frosting is achieved by a wider particle size distribution. Color bleeding or feathering is influenced by the amount of fines in the product, which also affect the staying power. Rheological properties determine coverage on the lips and how well it will flow when pressed (at varying pressures) on the lips.

When formulating an eye shadow, the particle size may influence the degree of frosting. Generally a cosmetically acceptable eye shadow may be defined as one that exhibits a fine particle size distribution, meaning that it is more likely to blend into the skin, to be more durable, and to prevent creasing in the fold of the eyelid. Rheological properties also help to determine optimum deposition quantity and thickness.

When formulating a foundation, the particle size of the foundation should not be so small that it can block up the pores, but should not be so large that it accentuates fine facial lines. Particle size analysis and rheology are particularly important in the analysis of fumed Silica (one of the major ingredients in soft gels and creams). The smaller the size, the greater the surface area and the less material required for the desired viscosity.

If the particle size of a blush is too large and rheological properties are not properly controlled, it will not spread well.

Exfoliants/facial scrubs generally contain abrasive agents. The particle size of the abrasive agent used will influence the degree of abrasiveness. The larger the particle size distribution, the more effective the agent is abrading dead skin. In more sensitive areas of the body such as the face, a finer particle size is often used.

The particle size distribution of nail varnish (also referred to herein as nail polish) influences the setting time and how chip proof and durable the nail varnish is. If the particle size is too large, flaws commonly known as "streaks" will appear in the nail varnish. Proper control of the rheological properties will enable good leveling and coverage of brush marks, ensuring a higher quality appearance.

Ideally, the colored cosmetic delivery systems and methods of delivery of the present invention incorporate Homeopathic Color Pigment Products, which act as a delivery system for the homeopathic agent therein. The color pigment products must be of sufficiently high purity and of sufficiently low toxicity to render them suitable for administration and should maintain the stability and bioavailability of the Homeopathic Complexes of the present invention so that the homeopathic agent(s) remain active and have a therapeutic affect when in contact with the skin.

In the make-up formulations of the present invention, the coloring agents impart color, opacity, or translucence that beautifies and enhances or conceal parts of the face. In nail polish formulations of the present invention the coloring agents beautify and enhance the nails and hide flaws. In the cream, lotion, serum, and scrub formulations of the present invention, such as sunscreen, eye cream, night lotion, facial serum and facial scrub, the coloring agents enable a user to determine where the product is being applied to ensure that full coverage is attained. In products which remain on the skin for a period of time, such as sunscreen, eye cream, night lotion and facial serum, color agents may be chosen which impart subtle color. In such embodiments, the homeopathic color complex comprises not more than about 5%, 10%, 15%, 20%, 25%, 30%, 35%, 40%, 45%, 50%, 55%, 60%, 65%, 70%, 75%, 80%, 85%, 90%, 95%, or 100% by weight of the formulation.

The coloring agents used in a particular formulation may first be contacted with selected homeopathic agents to create a Homeopathic Color Pigment Product, which then is utilized in the formulation of the chosen cosmetic. As used in this context, the term "contacted" refers to the state or condition of touching or being in immediate proximity. More specifically, it is used to describe the place or surface where a particle of the coloring agent and a Homeopathic Complex come together. Alternatively, the coloring agents may be contacted with the Homeopathic Complex(es) at the same time that they are mixed with other ingredients of the chosen cosmetic formulation.

The Homeopathic Complexes of the present invention may include two or more of the following homeopathic agents: Abrotanum (Southernwood), Aceticum acidum, (Glacial Acetic Acid), Aconitum napellus (Monkshood), Aesculus hippocastanum (Horse Chestnut), Aloe socotrina (Socotrine Aloes), Alumina (Oxide of Aluminum-Argilla), Ammonium benzoicum (Benzoate of Ammonia), Antimonium crudum (Black Sulphide of Antimony), Apis mellifica (Whole Honey Bee), Argentum nitricum (Nitrate of Silver), Arnica montana (Leopard's Bane), Arsenicum album (Arsenious Acid-Arsenic Trioxide), Azadirachta indica (Melia Azadirachta, Nim, Neem, Margosa), Baptisia tinctoria (Wild Indigo), Baryta carbonica (Carbonate of Baryta), Belladonna (Deadly Nightshade), Berberis aquifolium-Mahonia (Oregon Grape, Mountain Grape), Berberis vulgaris (Barberry), Borax veneta (Borate of Sodium), Bovista lycoperdon (Puff Ball), Bryonia alba (Wild Hops), Cactus grandiflorus-Selenicereus spinulosus (Night-blooming Cereus), Calcarea carbonica-ostrearum (Carbonate of Lime), Calcarea fluorica-Fluor spar (Fluoride of Lime), Calcarea phosphorica (Phosphate of Lime) Calcarea sulphurica (Sulphate of Lime), Camphora officinalis (Camphor), Candida albicans (yeast), Cantharis vesicatoria (Spanish Fly), Capiscum annuum (Cayenne Pepper), Carbo vegetabilis (Vegetable Carcoal), Carduus benedictus (Blessed Thistle), Carduus marianus (St. Mary's Thistle), Causticum (Hahnemann's Tinctura Acris Sine Kali), Chamomilla (German Chamomile), Chelidonium majus (Celandine, Tetterwort), Cholesterinum (Cholesterine—The Proximate Principle. Furnished by the Epithelium Lining of the Gall Bladder and Larger Ducts.), Chimicifuga racemosa—(Acteaea racemosa) (Macrotys) (Black Snake-root), Cinchona officinalis-China (Peruvian Bark), Coffea cruda (Unroasted Coffee), Comocladia dentate (Guao), Conium maculatum (Poison Hemlock), Crataegus oxyacantha (Hawthorn Berries), Crotalus horridu (Rattlesnake), Croton tiglium (Croton Oil Seed), Cunderango (Condor Plant), Curcuma longa, Dioscorea villosa (Wild Yam), Dulcamara (Bittersweet, species of Vine in Potato Genus Solanum, Family Solanaccae), Echinacea augustifolia-Rudbeckia (Purple Cone-flower), Echinacea purpurea (Purpose Cone-flower), Eclipta alba, Elaps corallinus (Coral-snake), Emblica officinialis, Eugenia jambos-Jambosa vulgaris (Rose-apple), Euphrasia officinalis (Eyebright), Euphorbium officinarum (Spurge—The Resinous Juice of Euphorbia Resinifera), Fluoricum acidum (Hydrofluoric Acid), Formica rufa (Myrmexine) (Crushed Live Ants), Fraxinus americana (White Ash), Fuligo ligni (Soot), Fumaria officinalis (Earth Smoke), Gelsemium sempervirens (Yellow Jasmine), Ginseng quinque folium (Aralia quinquelfolia-Wild Genseng-Panax), Glycyrrhiza glabra (Licorice Root), Granatum (pomegranate), Graphites (Black Lead-Plumbago), Grindelia robusta (Rosin-wood), Hamamelis virginiana (Witchhazel), Helleborus niger (Snow-rose), Hepar sulphuris calcareum (Calcium Sulfide of Hahnemann and Sulfur of Lime), Hippozaeninum (Gladerine-mallein-Farcine), Histaminum hydrochloricum, Hydrastis canadensis (Goldenseal Root), Hydrocotyle asiatica (Indian Pennywort), Hydrocyanicum acidum (Prussic Acid), Hypericum perforatum (St. John's Wort), Ignatia amara (St. Ignatius Bean), Iodium (Iodine), Iris versicolor (Blue Flag), Ferrum phosphoricum (Iron Phosphate), Juglans regia (Walnut), Juglans cinerea (Butternut), Juniperus communis (Juniper Berries), Kalium arsenicosum (Fowler's solution), Kalium bichromicum (Bichromate of Potash), Kalium bromatum (Bromide of Potash), Kalium carbonicum (Carbonate of Potassium), Kalium hydriodicum (Iodide of Potassium), Kalium muriaticum (Chloride of Potassium), Kalium phosphoricum (Phosphate of Potassium), Kallium sulphuricum (Potassiumn Sulfate), Kreosotum (Beechwood Kreosote), *Lachesis mutus* (Bushmaster or Surucucu), *Lappa arctilum* (Burdock), *Ledum palustre* (Marsh Tea, Wild Rosemary), *Lilium tigrinum* (Tiger Lily), Lithium carbonicum (Carbonate of Lithium), *Lycopodium clavatum* (Stag's Horn Club Moss or Ground Pine), *Lycopus virgincus* (Buggle weed), Magnesia muriatica (Magnesium Chloride), Magnesia carbonica (Carbonate of Magnesia), Magnesia phosphorica (Phosphate of Magnesia), *Magnolia grandifluora* (Magnolia), *Mancinella* (*Hippomane*-Manganeel Apple), Manganum aceticum (Manganese Acetate), Medussa (Jelly-fish), Mercurius cyanatus, Mercurius corrosives (Corrosive Sublimate), Mercurius dulcis (Calomel), Mercurius iodatus ruber (Bin-iodide of Mercury), Mercurius solubilis-hydragyrum (Quicksilver), Mezereum (Spurge Olive), *Murex purpurea* (Purple Fish), Morphinum (An Alkaloid of Opium), Muriaticum acidum (Muriatic Acid), Natrium arsenicosum (Arsenate of Sodium), Natrium carbonicum (Carbonate of Sodium), Nabal, Natrium hypochlorosum (Chlorate of Sodium—Labarraque's Solution), Natrium muriaticum (Chloride of Sodium), Natrium phosphoricum (Phosphate of Sodium), Natrium sulphuricum (Sulphate of Sodium—Galuber's Salt), Nitricum acidum (Nitric Acid), *Nux moschata* (Nutmeg), *Nux vomica* (Poison Nut), Oleander-*Nerium ordorum* (Rose laurel), Oleum jecoris aselli (Cod Liver Oil), Oopohrinum (Ovarian Extract), Opium-*Papaver somniferum* (Dried Latex of Poppy), Petroleum (Crude Rock-oil), Phosphorus, Phosphoricum acidum (Phosphoric Acid), Plumbum metallicum (Lead), *Podophyllum peltatum* (Mayapple), Kalium bromatum (Potassium Bromide), Kalium carbonicum (Potassium Carbonate), Psorinum (Scabies Vesicle), *Pulex irritans* (Common Flea), *Pulsatilla pratensis* (Wind Flower), Radium bromatum (Radium Bromide), *Rhus toxicodendron* (Poison Ivy), *Rumex crispus* (Yellow Dock), *Sanguinaria canadensis* (Bloodroot), Sanicula aqua (the Water of Sanicula Springs, Ottawa), *Sarsaparilla officinalis* (Smilax, Wild Licorice), *Secale cornutum-Claviceps purpurea* (Rye Ergot), Selenium metallicum (Metallic Selenium), *Sepia officinalis* (the Inky Juice of the Common or European Cuttlefish), Silicea terra (Silica, Pure Flint), *Spigelia anthelmia* (Pink Root, Annual Worm Grass), Staphysagria (Stavesacre), *Stramonium* (Thorn Apple, Jamestown Weed, Jimson Weed), Sulphur (Sublimated Sulfur), Sulphuricum acidum (Sulfuric Acid), Sulfur iodatum (Iodosulfane), *Taraxacum officinale* (Common Dandelion, Balloon Plant, Puff Ball), *Teucrium marum verum* (Cat Thyme), *Thuja occidentalis*, (White Cedar, Aarbor Vitae), *Urtica urens* (Dwarf Nettle, Small Stinging Nettle, Burning Nettle, Dog Nettle), *Veratrum album* (White Hellebore), *Verbascum thapsus* (Mullein), *Vipera berus* (European Adder; Common Viper, German Viper), and Zincum metallicum (Zinc).

In some embodiments, the Homeopathic Colored Pigment Products of the present invention are prepared by (1) preparing the Homeopathic Complex; (2) and spraying the Homeopathic Complex on at least one coloring agent in powder form. During the spraying process, the powders are stirred continually to maximize contact of the Homeopathic Complex with at least one surface of the particles in the plurality of particles of the coloring agent. The resulting powder is labeled with the degree of strength of the liquid attenuation used in its preparation. Where the homeopathic agent is a solid, a liquid attenuation according to HPUS or other applicable guidelines must be prepared as a first step.

The skilled artisan will appreciate that homeopathic agents used to prepare the Homeopathic Complex may be attenuated to a range of about 1X to about 50,000 Q. In some embodiments of the invention, the homeopathic agents are attenuated to about 1X, 3X, 6X, 8X, 10X, 15X, 30X, 3C, 6C, 30C, 100C or 200C. The skilled artisan will appreciate that higher attenuations, such as 100C to 50,000Q, often are desired for deeper and more subtle homeopathic treatment for long stranding, broad range, chronic disorders.

Any coloring agent that contains a plurality of particles having at least one surface that is suitable for use in cosmetics, i.e., on living skin, may be used in the present invention. Coloring agents commonly found in cosmetic formulations are set forth in Table 3 below. The quantities of coloring agents will vary depending on the shade and tint desired in the final product. All percentages are by weight.

TABLE 3

Coloring Agents

| Coloring Agent | Percent (%) By Weight |
| --- | --- |
| Mica | 0.00-100.0 |
| Titanium Dioxide | 0.00-90.0 |
| Iron Oxide | 0.00-80.0 |
| Ultramarine Blue | 0.00-90.0 |
| Zinc Oxide | 0.00-50.0 |
| Ferric Ferrocyanide | 0.00-90.0 |
| Clay | 0.00-20.0 |
| Serecite | 0.00-100 |
| Starch | 0.00-90.0 |

The term "astringent" as used herein refers to substances used to clean the skin and constrict the pores. Astringents aid in reducing oil on the skin and in oil control, and may be drying or non drying depending on the astringent used. Alcohol, witch hazel extract, hydrosols, and acids are common astringents.

In some embodiments, a formulation prepared according to the present invention may take the compositional form of a paste, a cream, a lotion, a powder, an ointment, or a gel.

In some embodiments, the compositional form is a paste, meaning a semisolid dosage form that contains one or more substances intended for topical application. Pastes generally are divided into fatty paste and those made from a single-phase aqueous gel.

In some embodiments, the compositional form is a cream. The term "cream" as used herein refers to a viscous liquid or semisolid emulsion of either the oil-in-water or water-in-oil type. As used herein "emulsion" refers to a colloid system in which both the dispersed phase and the dispersion medium are immiscible liquids where the dispersed liquid is distributed in small globules throughout the body of the dispersion medium liquid. A stable basic emulsion contains at least the two liquids and an emulsifying agent. Common types of emulsions are oil-in-water, where oil is the dispersed liquid and an aqueous solution, such as water, is the dispersion medium, and water-in-oil, where, conversely, an aqueous solution is the dispersed phase. It also is possible to prepare emulsions that are nonaqueous. Creams of the oil-in-water type include hand creams and foundation creams. Water-in-oil creams include cold creams and emollient creams. The term "emollient" as used herein refers to fats or oils in a two-phase system (meaning one liquid is dispersed in the form of small droplets throughout another liquid). Emollients soften the skin by forming an occlusive oil film on the stratum corneum, preventing drying from evaporation in the deeper layers of skin. Thus, emollients are employed as protectives and as agents for softening the skin, rendering it more pliable. Emollients also serve as vehicles for delivery of hydrophobic compounds. Common emollients used in the manufacture of cosmetics include, but are not limited to, butters, such as Aloe Butter, Almond Butter, Avocado Butter, Cocoa Butter, Coffee Butter, Hemp Seed Butter, Kokum Butter, Mango Butter, Mowrah Butter, Olive Butter, Sal Butter, Shea Butter, glycerin, and oils, such as Almond Oil, Aloe Vera Oil, Apricot Kernel Oil, Avocado Oil, Babassu Oil, Black Cumin Seed Oil, Borage Seed Oil, Brazil Nut Oil, Camellia Oil, Castor Oil, Coconut Oil, Emu Oil, Evening Primrose Seed Oil, Flaxseed Oil, Grape Seed Oil, Hazelnut Oil, Hemp Seed Oil, Jojoba Oil, Kukui Nut Oil, Macadamia Nut Oil, Meadowfoam Seed Oil, Mineral Oil, Neem Seed Oil, Olive Oil, Palm Oil, Palm Kernel Oil, Peach Kernel Oil, Peanut Oil, Plum Kernel Oil, Pomegranate Seed Oil, Poppy Seed Oil, Pumpkin Seed Oil, Rice Bran Oil, Rosehip Seed Oil, Safflower Oil, Sea Buckthorn Oil, Sesame Seed Oil, Shea Nut Oil, Soybean Oil, Sunflower Oil, Tamanu Oil, Turkey Red Oil, Walnut Oil, Wheatgerm Oil Creams may be diluted only with suitable diluents specified in the appropriate entries, and diluted creams must be freshly prepared without the application of heat. Creams should be stored in a cool place and supplied in well-closed containers that prevent evaporation and contamination of the contents. When making a natural cream, however, butters first are melted. The vessel is removed from the heat and the oils are added. When the solution is 100 degrees F., the balance of the liquid portion of the formula then is slowly added while continuously stirred.

In some embodiments, the compositional form is a lotion, meaning a liquid or semi-liquid preparation that contains one or more active ingredients in an appropriate vehicle. A lotion may be a suspension of solids in an aqueous medium, an emulsion, or a solution.

A "solution" generally is considered as a homogeneous mixture of two or more substances. It is frequently, though not necessarily, a liquid. In a solution, the molecules of the solute (or dissolved substance) are uniformly distributed among those of the solvent. Solvents that may be useful in the compositions of the present invention include water, as well as organic solvents, such as the alcohols.

In some embodiments, the compositional form is a powder, also referred to as a dusting powder. The fineness of a powder often is expressed in terms of mesh size. Powders seeking to avoid any sensation of grittiness generally have a particle size of not more than 150 µm, i.e., less than 100-mesh.

In some embodiments, the compositional form is an ointment. An ointment is a semi-solid preparation often intended for external application to the skin. Generally, ointment bases are categorized into hydrocarbon bases (oleaginous), adsorption bases (anhydrous); emulsion bases (water and oil type); and water soluble bases. Due to their anhydrous nature, ointments generally do not require any preservatives. They are more moisturizing and more occlusive than creams, and form a protective film over the skin. The occlusive effect tends to prolong and enhance penetration.

In some embodiments, the compositional form of the present invention is a gel. The term "gel" as used herein refers to a sticky, jelly-like semisolid or solid prepared from high molecular weight polymers in an aqueous or alcoholic base. Alcoholic gels are drying and cooling, and are best suited for acute exudative pruritic eruptions; non-alcoholic gels are more lubricating and are well suited, for example, to dry scaling lesions. Due to their drying effect, especially from those gels containing alcohol, they may cause irritation and cracking of the skin. Starches and aloe are commonly used agents in the manufacture of gelled cosmetic preparations.

Additional compositional forms may be prepared using technology readily known in the cosmetic arts, such as described in Remington: The Science and Practice of Pharmacy, 20th Ed. (Gennaro, A. R. et al., eds) Lippincott Williams & Wilkins: Philadelphia (2000), which is incorporated herein by reference.

As used herein, the term "health" refers to a subject's general sense of well-being, and the term "heal" or "healing" refer to the restoration of health or wholeness. It is to be understood that a subject's sense of well-being may be one that is perceived only as such by the subject using the inventive compositions.

As used herein, the term "homeopathic color complex" refers to the complex formed by contacting a coloring agent and a Homeopathic Complex.

As used herein, the terms "homeopathically effective amount," and "effective amount" are used interchangeably to refer to the amount of the composition of the invention that results in a therapeutic or beneficial effect, including a subject's perception of health or general well-being, following its administration to a subject.

The term "humectants" as used herein refers to substances that promote water retention due to their hygroscopicity. They act by being absorbed into the skin and attract water from the atmosphere. The attracted water then serves as a reservoir for the stratum corneum.

The terms "hydrosol" "floral waters", "hydroflorales", "flower waters" or "distillates" are used interchangeably herein to refer to the liquid remaining in the still after steam distillation of an essential oil. Hydrosols contain all of the essence of the plant in every drop, just like essential oils, but in a milder form, making them suitable for all manner of applications where essential oils might otherwise be too strong. The chemical components in the hydrosol are primarily acids, which are hydrophilic. Because they acidify the water or the product in which they are used, hydrosols act as healing anti-inflammatory agents and mild, but therapeutic, antiseptics. Because acidic environments are astringent, hydrosols are useful in skin care products to constrict and contract the tissues. Examples of hydrosols useful in the present invention include, but are not limited to Angelica Hydrosol, Basil Hydrosol, Calendula Hydrosol, Chamomile Hydrosol, Cardamom Hydrosol, Cedar Leaf (*Thuja*) Hydrosol, Cinnamon Hydrosol, Clary Sage Hydrosol, Clove Hydrosol, Cucumber Hydrosol, Cypress Hydrosol, Eucalyptus Hydrosol, Grapefruit Hydrosol, Helichrysum Hydrosol, Jasmine Hydrosol, Juniperberry Hydrosol, Katrafay Hydrosol, Lavender Hydrosol, Lemongrass Hydrosol, Lemon Balm Hydrosol, Lemon Verbena Hydrosol, Lime Hydrosol, Melissa Leaf Hydrosol, Myrtle Hydrosol, Neroli Hydrosol, Oregano Hydrosol, Parsley Hydrosol, Peppermint Hydrosol, Petitgrain Hydrosol, Ponderosa Pine Hydrosol, Ravensara Hydrosol, Rose Hydrosol, Rose Geranium Hydrosol, Rosemary Hydrosol, Sandalwood Hydrosol, Spearmint Hydrosol, Spikenard Hydrosol, Tarragon Hydrosol, Tea Tree Hydrosol, Thyme Hydrosol, Yarrow Hydrosol, Ylang ylang Hydrosol The term "preservative" is used herein to refer to substances that prevent the growth of undesired microorganisms in products that contain water. Preservatives approved for use in cosmetics may be identified in the current Federal Regulations published in volume 21 of the Code of Federal Regulations, which is incorporated herein by reference. Preservatives useful in the present invention include, but are not limited to: ascorbic acid, ascorbyl palmitate, Biopein, BHT (butylated hydroxyl-toluene), butylated hydroxyanisole, butylated hydroxytoluene, butylparaben, calcium ascorbate, calcium sorbate, citric acid, cinnamon cassia, chlorocresol, diazolidinyl urea, dilauryl thiodipropionate, EDTA (ethylenediamine tetraacetic acid tetrasodium salt), erythorbic acid, grapefruit seed extract, hydroxyhenzoates, methylparaben, Neopein, phenonip, phenoxyethanol, potassium bisulfite, potassium metabisulfite, potassium sorbate, propylparaben, rosemary oil extract, sodium ascorbate, sodium benzoate, sodium bisulfite, sodium metabisulfite, sodium sorbate, sodium sulfite, sorbic acid, sulfur dioxide, Suprarein, thiodipropionic acid, and/or tocopherols.

As used herein, the terms "preventing", "prevent," or "prevention of", refer to the keeping from happening, anticipating or countering in advance a condition or symptoms of a condition, including the appearance of esthetical symptoms of a condition, protecting from harmful or annoying stimuli, or generally promoting health. As used herein, the terms "promoting", "promote", or "promotion" of includes contributing to, furthering, helping, or maintaining health.

The term "suspension" as used herein refers to preparations of finely divided, undissolved substances dispersed in liquid vehicles. The particulate matter of a suspension may settle slowly from the liquid vehicle in which it is dispersed; therefore, suspensions should be shaken well before use to ensure uniform distribution of solid in the vehicle and thereby uniform and proper dosage.

Cosmetic formulations routinely are applied to the face and other areas of the skin and often remain on the skin for extended periods of time. Cosmetics may be formulated as foundations, pressed powders, loose powders, setting powders, blushes, rouges, eye shadows, mascaras, eye brow liners, eye brow pencils, concealers, lipsticks, lip glosses, lip liners, lip pencils, eye liners, eye pencils, nail polishes, lip moisturizers, lip exfoliators, bronzers, body and facial scrubs, eye creams, facial creams, toners, eye brow enhancers, sunscreens, and other like agents that are intended to beautify the wearer by providing color, contrast or otherwise changing or enhancing the appearance of the skin. Commonly, cosmetics are used as part of a routine skin care and makeup program on a daily basis. Many references exist for teaching how to create acceptable formulations of cosmetics, one of which is Handbook of Cosmetic Science and Technology, Second Edition, Marc Paye, et al. (Editor), CRC Press (2006), which is expressly incorporated herein by reference.

The formulations of the present invention may be based on any agent capable of being accepted by a regulatory body such as the United States Food and Drug Administration for use in cosmetics or drugs. It is believed that the use of natural ingredients enhances delivery and promotes better health and wellness of the user. Examples of acceptable agents useful for formulating the cosmetics of the present invention include but are not limited to: *aloe vera* gel, almond flour, almond oil, aloe powder, antioxidants, apricot kernel oil, arrowroot powder, beeswax, bentonite clay, boron nitride, brown sugar, candelilla wax, carnation mineral oil, carnauba wax, chamomile extract, castor oil, citric acid, clay, cloisonne, cocoa butter, coconut milk, coconut oil, coconut water, corn starch, dried flowers, emery, emulsifying wax, epsom salt, essential oils, ferric ferrocyanide, flameco twilight, French green clay, fullers earth clay, glycerin, glycerin stearate, grain alcohol, grape seed oil, guar gum, hazelnut oil, herbal teas, herbal oils, honey, hydrogenated lanolin, hydrosols, iron oxide, isoeicosane, isohexacontane permethyl, isopropylan 33 (lanolin oil), isopropyl lanolate, isopropyl myristate, isosteric acid, jasmine grandiflorum wax, jasmine sambac wax, jojoba oil, jojoba wax flakes, kaolin clay, kokum butter, kukui nut oil, lanolin anhydrous, lecithin, lemon peel, lexemul, mango butter, meadowfoam seed oil, mearlmica, mearlite, mica, milk powder, mimosa wax, mineral oil, miglyol, oatmeal flour, olive oil, orange peel, petroleum distillate, polyurethane, potassium sorbate, propylene glycol, propylparaben, pumpkin seed oil, purified water, rhassoul clay, rosehip seed oil, rose wax, safflower oil, sal butter, salt, saponified oils, serecite, sesame oil, shea butter, silk powder, sodium benzoate, starch, steric acid, sunflower oil, a natural preservative, such as Suprarein™ (a non-paraben preservative derived from essential oils), Biopein (an all natural preservative and stabilizing ingredient manufactured from a blend of botanical extracts), and Neopein®, talc, tamanu oil, timica, titanium dioxide, tretholamine, ultramarine (blue, green, pink, red, violet), vitamin E, water, water miscible acrylic, witch hazel, witch hazel extract, wheat germ oil, zinc oxide, and zinc stearate.

"Essential oils" are any volatile oils obtained from plants that possess the odor and other characteristics properties of the plant. Essential oils useful in the present invention include, but are not limited to: Basil, Bergamot, Blue Cypress, Cajeput, Cardamom, Carrot Seed, Cassia, Catnip, Chamomile, Clary Sage, Clove Bud, Cedarwood, Cinnamon, Coffee, Cognac (Green), Coriander, Cumin, Cypress, Eucalyptus (lemon), Eucalyptus, Fennel, Foraha, Frankincense, Geranium, German Chamomile, Grapefruit, Helichrysum, Hyssop, Jasmine, Juniperberry, Lavender, Lemon, Lemongrass, Lime, Litsea cubeba, Mandarin, Myrrh, Neem Seed, Neroli, Orange, Patchouli, Pepper (Black), Peppermint, Roman Chamomile, Rose, Rosehip, Rosemary, Rosewood, Sandalwood, Spearmint, Spruce, St. John's Wort, Tangerine, Tea Tree, Thyme, Valerian, Vetiver, Violet, and/or Ylang Ylang.

The term "subject" as used herein includes animals of mammalian origin, including humans.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein may also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication where provided may be different from the actual publication dates, which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Fahrenheit, and pressure is at or near atmospheric.

Homeopathic Color Pigment Products for Use on Various Types of Skin.

The homeopathic agents useful in formulating the Homeopathic Color Pigment Products of the present invention may include any known or foreseeable homeopathic agent. Homeopathic agents may be found in various references including, but not limited to: Lennon, Nigey, and Lionel Rolfe. Homeopathic Cell Salt Remedies, Healing with Nature's Twelve Mineral Compounds. Garden City Park: Square One, 2004. 1-155, Boericke, William. New Manual of Homoeopathic Materia Medica & Repertory. Ninth ed. New Delhi: B. Jain (P.) LTD, 2005. 1-1319, Homeopathic Pharmacopoeia Convention of the United States/Revision Service; WDC: Pharmacopoeia Convention of the Amerimay Institute of Homeopathy, 1988. HPRS-2003-45, Frans Vermeulen, Concordant Materia Medica, Emryss Publishers, Millenium edition November 2000; Margarethe Harrms, Homöopathische Mittel und ihre Wirkungen Materia Medica und Repertorium), Verlag Grundlagen und Praxis (publisher), Leer (1973); Drs Léon Vannier & Jean Poirier; Précis de Matiére Medicale Homoepathique 8th Edition Revue Corrigee et Augmentée; 8, Place de L'Odéon, Paris (1968); Timothy F. Allen; Ed., and The Encyclopedia of Pure Materia Medica, B Jain Publishers; 55/I Arjua Nagar, New Delhi (1976), all of which expressly are incorporated herein by reference. Non-limiting examples of homeopathic agents are set forth on Tables 1 and 2 herein.

The following description sets forth five Homeopathic Complexes. Homeopathic Complexes considered as part of the present invention may be formulated in attenuations and successions ranging from about 1X to about 50,000Q.

In some embodiments, Homeopathic Complex 1 formulated for inclusion in cosmetics for use on normal skin comprises Calcarea fluorica-Fluor spar (Calcium fluoride), Calcarea phosphorica (Calcium phosphate), Calcarea sulphurica (Calcium sulfate), Ferrum phosphoricum (Iron phosphate), Kalium carbonicum (Potassium chloride), Kalium phosphoricum (Potassium phosphate), Kalium sulphuricum (Potassium sulfate), Magnesia phosphorica (Magnesium phosphate), Natrium muriaticum (Sodium chloride), Natrium phosphoricum (Sodium phosphate), Natrium sulphuricum (Sodium sulfide) and Silicea terra (Silica). In other embodiments, a Homeopathic Complex 1 formulation optionally includes at least one of the following: *Azadirachta indica, Glycyrrhiza glabra, Carduus benedictus, Carduus marianus, Juniperus communis, Taraxacum officinale*. In some embodiments, Homeopathic Complex 1 may include at least one of: *Centella asiatica, Curcuma longa, Eclipta alba, Emblica officialis, Terminalia belerica*, and *Terminalia chebula*.

One embodiment of Homeopathic Complex 1 is set forth in Table 4. A skilled artisan will recognize that while this embodiment shows that each ingredient of Homeopathic Complex 1 is mixed in equal proportion with each of the other ingredients, the ingredients of Homeopathic Complex 1 may be mixed in nonequal/different proportions for specific needs, and that each homeopathic agent in the Homeopathic Complex may be formulated in attenuations and successions ranging from about 1X to about 50,000Q.

TABLE 4

| Homeopathic Complex 1 | |
|---|---|
| Active Agent | Attenuation and Succussion |
| Calcarea fluorica - Fluor spar (Calcium fluoride) | 1X-20X |
| Calcarea phosphorica (Phosphate of Lime, Calcium phosphate) | 1X-20X |
| Calcarea sulphurica (Sulphate of Lime - Plaster of Paris, Calcium sulfate) | 1X-20X |
| Ferrum phosphoricum (Iron phosphate) | 1X-20X |
| Kalium muriaticum (Chloride of Potassium, Potassium chloride) | 1X-20X |
| Kalium phosphoricum (Phosphate of Potassium, Potassium phosphate) | 1X-20X |
| Kalium sulphuricum (Potassium sulfate) | 1X-20X |
| Magnesia phosphorica (Phosphate of Magnesia, Magnesium phosphate) | 1X-20X |
| Natrium muriaticum (Sodium chloride) | 1X-20X |
| Natrium phosphoricum (Phosphate of Sodium, Sodium phosphate) | 1X-20X |
| Natrium sulphuricum (Sulphate of Sodium - Glauber's Salt, Sodium sulfate) | 1X-20X |
| Silicea terra (Silica, Pure Flint) | 1X-20X |
| *Azadirachta indica* (Melia Azadirachta, Nim, Neem, Margosa) | 1X-20X |
| *Glycyrrhiza glabra* (Licorice Root) | 1X-20X |
| *Carduus benedictus* (Blessed Thistle) | 1X-20X |
| *Carduus marianus* (St. Mary's Thistle) | 1X-20X |
| *Juniperus communis* (Juniper Berries) | 1X-20X |
| *Taraxacum officinale* (Dandelion, Balloon) | 1X-20X |

Although Homeopathic Complex 1 may be used for any purpose for which any one of the individual homeopathics is known to have utility, the combination of homeopathics in the Complex is believed to create a synergistic effect. Homeopathic Complex 1 is useful for preventative maintenance, to reduce damage to the skin, and/or to enhance the body's ability to use key minerals that promote good health and immunity from disease. Homeopathic Complex 1 prevents wellness problems from arising by helping the body stay well balanced and maintained. It also prevents and mitigates damage caused by stress and toxins, including but not limited to those found in bacteria and viruses. It protects against environmental factors, such as damage cause by sun exposure, air pollution, preservatives, dyes, pesticides, and toxic chemicals (such as cleaning agents and detergents), nourishes the skin, and supports the body's ability to cope with climatic variations.

Homeopathic Complex 2

"Problem skin" as used herein, refers to skin that has a condition that is unrelated to natural aging symptoms. Problem skin includes, but is not limited, skin that displays the symptoms of acne, pimples, pustules, boils, eczema, psoriasis, hives or hot, burning, red, swollen, inflamed, sensitive or rashy skin. Any skin disorder that requires intervention to resolve it may be indicative of problem skin.

Homeopathic Complex 2 formulated for inclusion in cosmetics for problem skin comprises *Antimonium crudum, Apis mellifica, Dulcamara*, Graphites, Kalium bromatum, *Ledum palustre, Rhus toxicodendron, Berberis aquifolium-Mahonia, Lappa arctium*, and *Sarsaparilla officinalis*. In some embodiments, the formulation optionally includes at least one of the following: *Bovista lycoperdon, Candida albicans, Gelsemium sempervirens*, Mezereum, *Stramonium*, Sulfur iodatum, *Echinacea augustifolia-Rudbeckia, Fumaria offici-* nalis, *Hydrocotyle asiatica, Juglans regia, Taraxacum officinale, Rumex crispus*, and *Urtica urens*.

Problem skin may require additional and/or other active agents that may be in different proportions than those found in other Homeopathic Complexes of the present invention. One embodiment of Homeopathic Complex 2 is set forth in Table 5. A skilled artisan will recognize that while this embodiment shows that each ingredient of Homeopathic Complex 2 is mixed in equal proportion with each of the other ingredients, the ingredients of Homeopathic Complex 2 may be mixed in nonequal/different proportions for specific needs. Moreover, a skilled artisan will recognize that each homeopathic agent in the Homeopathic Complex may be formulated in attenuations and successions ranging from about 1X to about 50,000Q.

TABLE 5

Homeopathic Complex 2

| Active Agent | Attenuation and Succussion |
| --- | --- |
| Antimonium crudum | 1X-20X |
| *Apis mellifica* | 1X-20X |
| *Bovista lycoperdon* | 1X-20X |
| *Candida albicans* | 1X-20X |
| *Dulcamara* | 1X-20X |
| *Gelsemium sempervirens* | 1X-20X |
| Graphites | 1X-20X |
| Kalium bromatum | 1X-20X |
| *Ledum palustre* | 1X-20X |
| *Mezereum* | 1X-20X |
| *Rhus toxicodendron* | 1X-20X |
| *Stramonium* | 1X-20X |
| Sulfur iodatum | 1X-20X |
| *Berberis aquifolium* - Mahonia | 1X-20X |
| *Echinacea augustifolia* - Rudbeckia | 1X-20X |
| *Fumaria officinalis* | 1X-20X |
| *Hydrocotyle asiatica* | 1X-20X |
| *Juglans regia* | 1X-20X |
| *Lappa arctium* | 1X-20X |
| *Taraxacum officinale* | 1X-20X |
| *Rumex crispus* | 1X-20X |
| *Sarsaparilla officinalis* | 1X-20X |
| *Urtica urens* | 1X-20X |

Although Homeopathic Complex 2 may be used for any purpose for which any one of the individual homeopathics is known to have utility, the combination of homeopathics in the Complex is believed to create a synergistic effect. It is useful for healing the skin, for preventing commonly occurring chronic or acute skin problems such as acne, pimples, eczema, rosacea, and other rash like eruptions; treatment of dry, oily, itchy, or irritated skin; balancing and evening out the color and texture of the skin; reduction of inflammation, pain or stinging in the skin, and promoting healthy lustrous skin through regulating healthy cellular activity.

Homeopathic Complex 3

In some embodiments, a formulation comprising Homeopathic Complex 3 is used to combat the effects of aging. In one embodiment, a formulation of Homeopathic Complex 3 for inclusion in cosmetics for prevention of aging skin comprises: Arsenicum album, Cactus grandiflorus-*Selenicereus spinulosus, Chelidonium majus*, Cholesteriunum, Kalium phosphoricum, Natrium muriaticum, *Podophyllum peltatum, Sepia officinalis*, Silicea terra (silicon dioxide, silicic anhydride, anhydrous silicic acid), and *Spigelia anthelmia*. In some embodiments, the formulation optionally includes at least one of the following: Calcarea sulphuria, *Conium maculatum*, Ferrum phosphoricum, Hepar sulphuris calcareum, *Hydrastis canadensis*, Kalium carbonicum, Kalium sulphuricum, *Lilium tigrinum, Lycopodium clavatum*, Magnesia muriatica, and Selenium metallicum.

One embodiment of Homeopathic Complex 3 is set forth in Table 6. A skilled artisan will recognize that while this embodiment shows that each ingredient of Homeopathic Complex 3 is mixed in equal proportion with each of the other ingredients, the ingredients of Homeopathic Complex 3 may be mixed in nonequal/different proportions for specific needs. For example, aging skin may require additional ingredients and/or different proportions. Moreover, a skilled artisan will recognize that each homeopathic agent in the Homeopathic Complex may be formulated in attenuations and successions ranging from about 1X to about 50,000Q.

TABLE 6

Homeopathic Complex 3

| Active Agent | Attenuation and Succussion |
| --- | --- |
| Arsenicum album | 1X-20X |
| *Cactus grandiflorus - Selenicereus spinulosus* | 1X-20X |
| Calcarea sulphurica | 1X-20X |
| *Chelidonium majus* | 1X-20X |
| *Cholesteriunum* | 1X-20X |
| *Conium maculatum* | 1X-20X |
| Ferrum phosphoricum (Iron phosphate) | 1X-20X |
| Hepar sulphuris calcareum | 1X-20X |
| *Hydrastis canadensis* | 1X-20X |
| Kalium carbonicum (Potassium carbonate) | 1X-20X |
| Kalium phosphoricum (Potassium phosphate) | 1X-20X |
| Kalium sulphuricum (Potassium sulfate) | 1X-20X |
| *Lilium tigrinum* | 1X-20X |
| *Lycopodium clavatum* | 1X-20X |
| Magnesia muriatica | 1X-20X |
| Natrium muriaticum (Sodium chloride) | 1X-20X |
| *Podophyllum peltatum* | 1X-20X |
| Selenium metallicum (Selenium) | 1X-20X |
| *Sepia* officinalis | 1X-20X |
| Silicea terra (Silica) | 1X-20X |
| *Spigelia anthelmia* | 1X-20X |

Although Homeopathic Complex 3 may be used for any purpose for which any one of the individual homeopathics is known to have utility, the combination of homeopathics in the Complex is believed to create a synergistic effect. It is useful for stopping degenerative changes in the skin, fading away age lines, promoting healthy cellular activity, moisturizing the skin and improving suppleness and elasticity, balancing and evening out the complexion, reducing the appearance of age spots, promoting a youthful, vibrant appearance, reducing imperfections in the skin, reducing the appearance of superficial veins, and mitigating pain caused by reduced skin hydration.

Homeopathic Complex 4

Formulations of the present invention also are useful to treat problem nails. In one embodiment, a formulation for inclusion in cosmetics useful for treating nails comprises Homeopathic Complex 4, comprising Alumina, *Antimonium crudum*, Fluoricum acidum, Graphites, Nitricum acidum, *Sepia officinalis*, Silicea terra, Sulphuricum acidum, *Teucrium marum verum*, and *Thuja occidentalis*. In some embodiments, the formulation optionally includes at least one of the following: Arsenicum album, *Bryonia alba, Candida albicans, Discorea villosa, Dulcamara, Echinacca purpurea*, Hepar sulphuris calcareum, Kalium carboncum, *Lachesis mutus, Lycopodium clavatum*, Mezereum, Phosphorus, and Zincum metallicum.

One embodiment of Homeopathic Complex 4 is set forth in Table 7. A skilled artisan will recognize that while this embodiment shows that each ingredient of Homeopathic Complex 4 is mixed in equal proportion with each of the other ingredients, the ingredients of Homeopathic Complex 4 may be mixed in nonequal/different proportions for specific needs. For example, problem nails may require additional ingredients and/or different proportions. Moreover, a skilled artisan will recognize that each homeopathic agent in the Homeopathic Complex may be formulated in attenuations and successions ranging from about 1X to about 50,000Q.

TABLE 7

Homeopathic Complex 4

| Active Agent | Attenuation and Succession |
| --- | --- |
| Alumina | 1X-20X |
| Antimonium crudum | 1X-20X |
| Arsenicum album | 1X-20X |
| Bryonia alba | 1X-20X |
| Candida albicans | 1X-20X |
| Dioscorea villosa | 1X-20X |
| Dulcamara | 1X-20X |
| Echinacea purpurea | 1X-20X |
| Fluoricum acidum | 1X-20X |
| Graphites | 1X-20X |
| Hepar sulphuris calcareum | 1X-20X |
| Kalium carbonicum (Potassium carbonate) | 1X-20X |
| Lachesis mutus | 1X-20X |
| Lycopodium clavatum | 1X-20X |
| Mezereum | 1X-20X |
| Nitricum acidum | 1X-20X |
| Phosphorus | 1X-20X |
| Sepia officinalis | 1X-20X |
| Silicea terra | 1X-20X |
| Sulphuricum acidum | 1X-20X |
| Teucrium marum verum | 1X-20X |
| Thuja occidentalis | 1X-20X |
| Zineum metallicum | 1X-20X |

Although Homeopathic Complex 4 may be used for any purpose for which any one of the individual homeopathics is known to have utility, the combination of homeopathics in the Complex is believed to create a synergistic effect. It is useful for strengthening brittle, weak nails, to relieve a gnawing feeling under the nail and other sensitivities of the nail, for treatment of white spots on the nail, for treatment of suppurated grooves in the nails and ridges, and for the treatment and prevention of hang nails.

Homeopathic Complex 5

In some embodiments, a formulation of Homeopathic Complex 5 for inclusion in cosmetics for prevention of sun damage comprises *Aconitum napellus, Apis mellifica, Belladonna, Cantharis vesicatoria, Cinchona officinalis*-China, Ferrum phosphoricum, Kalium muriaticum, Radium bromatum, *Sanguinaria canadensis*, and *Urtica urens*. In some embodiments, the formulation optionally includes at least one of the following: Aceticum acidum, Arsenicum album, *Baptisia tinctoria, Capsicum annuum*, Causticum, *Echinacea augustifolia, Euphorbium officinarum, Grindelia robusta, Hypericum perforatum*, Kalium carbonicum, Natrium muriaticum, *Nux vomica, Rhus toxicodendron, Secale cornutum-Claviceps purpurea*, and Sulphur.

One embodiment of Homeopathic Complex 5 is set forth in Table 8. A skilled artisan will recognize that while this embodiment shows that each ingredient of Homeopathic Complex 5 is mixed in equal proportion with each of the other ingredients, the ingredients of Homeopathic Complex 5 may be mixed in nonequal/different proportions for specific needs. For example, prevention of sun damage may require additional ingredients and/or different proportions. Moreover, a skilled artisan will recognize that each homeopathic agent in the Homeopathic Complex may be formulated in attenuations and successions ranging from about 1X to about 50,000Q.

TABLE 8

Homeopathic Complex 5

| Active Agent | Attenuation and Succession |
| --- | --- |
| Aceticum acidum | 1X-20X |
| Aconitum napellus | 1X-20X |
| Apis mellifica | 1X-20X |
| Arsenicum album | 1X-20X |
| Baptisia tinctoria | 1X-20X |
| Belladonna | 1X-20X |
| Cantharis vesicatoria | 1X-20X |
| Capsicum annuum | 1X-20X |
| Causticum | 1X-20X |
| Cinchona officinalis - China | 1X-20X |
| Echinacea augustifolia | 1X-20X |
| Euphorbium officinarum | 1X-20X |
| Ferrum phosphoricum (Ferrum phosphate) | 1X-20X |
| Grindelia robusta | 1X-20X |
| Hypericum perforatum | 1X-20X |
| Kalium carbonicum (Potassium carbonate) | 1X-20X |
| Kalium muriaticum (Potassium chloride) | 1X-20X |
| Natrium muriaticum (Sodium chloride) | 1X-20X |
| Nux vomica | 1X-20X |
| Radium bromatum | 1X-20X |
| Rhus toxicodendron | 1X-20X |
| Sanguinaria Canadensis | 1X-20X |
| Secale cornutum - Claviceps purpurea | 1X-20X |
| Sulphur | 1X-20X |
| Urtica urens | 1X-20X |

Although Homeopathic Complex 5 may be used for any purpose for which any one of the individual homeopathics is known to have utility, the combination of homeopathics in the Complex is believed to create a synergistic effect. It is useful for preventing sun burn, inflammation, sensitiveness and itching of the skin, allergic reactions, and ill effects due to sun exposure including heat, discoloration, dryness, soreness, bumps on skin, swelling or puffing up, stinging, pain, headaches, epithelioma, blistering, peeling, fever and dehydration, irritability, weakness, and exhaustion.

Cosmetic Compositions Containing Homeopathic Color Pigment Products.

Cosmetic compositions of the present invention contain a cosmetic base and at least one Homeopathic Complex comprising at least two homeopathic formulations as an active ingredient.

The cosmetic base of the Cosmetic Compositions of the present invention is formulated in a conventional manner. Depending on the formulation, the active homeopathic agents may be added in the normal course of formulating the product. In many instances however, the active homeopathic agents must be formulated separately and added at particular steps during manufacture of the final product or during the steps of manufacturing a subcomponent of the formulation. Thus, for liquid cosmetic products, the active ingredient is added into the batch production mixture at some point during the manufacturing process. For powders, the Homeopathic Complex active ingredient is applied by a spraying technique.

Example 1

Cream Foundation

A homeopathic cream foundation is a homeopathic topical solution formulated for the delicate and highly susceptible skin of the face. The facial skin's inherent constitution and quality of thinness provides an optimal high rate of absorption, one of the highest rates on skin found on the human body. In one embodiment, a foundation formulated according to the present invention incorporates an inactive base of oils, which act as the carrier that enables the active ingredients to gain access into and through the epidermis.

In one embodiment, the cream foundation containing Homeopathic Complex 1 of Table 4 is formulated in accordance with Table 9 below. All percentages are by weight.

TABLE 9

Cream Foundation

| Ingredient | Percentage (%) by Weight |
| --- | --- |
| Butter | 22.6-34.0 |
| Oil | 17.8-36.0 |
| Homeopathic Complex | 4.1-8.4 |
| Grain Alcohol | 0.6-2.6 |
| Preservative | 0.3-1.7 |
| Essential Oil | 0.2-1.4 |
| Coloring Agent | 28.4-42.6 |

In one embodiment of a cream foundation formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least starch. In another embodiment, the coloring agent comprises at least serecite.

In one embodiment, a homeopathic cream foundation for normal skin comprises Homeopathic Complex 1. In one such embodiment, the butter ingredient comprises Shea butter. In one such embodiment, the oil ingredient comprises Coconut oil. In one such embodiment, the oil ingredient comprises Grape Seed oil. In one such embodiment, the oil ingredient comprises Almond oil. In one such embodiment, the oil ingredient comprises Castor Oil. In one such embodiment the essential oil ingredient comprises Lavender. In one such embodiment the essential oil ingredient comprises Ylang Ylang. In one such embodiment the essential oil ingredient comprises Chamomile. In one such embodiment the essential oil ingredient comprises Geranium. In one such embodiment the essential oil ingredient comprises Frankincense. In one such embodiment the essential oil ingredient comprises Rose. A skilled artisan will recognize that other homeopathic agents, coloring agents, preservatives, butters, oils and essential oils may be used.

In one embodiment, a cream foundation for problem skin comprises Homeopathic Complex 2. In one such embodiment, the butter ingredient comprises Shea butter. In one such embodiment, the oil ingredient comprises Coconut oil. In one such embodiment, the oil ingredient comprises Grape Seed oil. In one such embodiment, the oil ingredient comprises Avocado oil. In one such embodiment, the oil ingredient comprises Castor Oil. In one such embodiment, the essential oil ingredient comprises Lavender. In one such embodiment, the essential oil ingredient comprises Geranium. In one such embodiment, the essential oil ingredient comprises Sandalwood. In one such embodiment, the essential oil ingredient comprises Myrrh. In one such embodiment, the essential oil ingredient comprises Frankincense. In one such embodiment, the essential oil ingredient comprises Chamomile. In one such embodiment, the essential oil ingredient comprises Rosehip Seed. A skilled artisan will recognize that other homeopathic agents, coloring agents, preservatives, butters, oils and essential oils may be used.

In yet another embodiment useful for aging skin, Homeopathic Complex 3 is substituted for Homeopathic Complex 1. The cream foundation for aging skin comprises Homeopathic Complex 3. In some such embodiments, the butter ingredient comprises Shea butter. In some such embodiments, the butter ingredient comprises Kokum butter. In some such embodiments, the oil is Grape seed oil. In some such embodiments, the oil ingredient comprises Avocado oil. In some such embodiments, the oil ingredient comprises Hazelnut oil. In some such embodiments, the oil ingredient comprises Almond oil. In some such embodiments, the oil ingredient comprises Pumpkin seed oil. In some such embodiments, the oil ingredient comprises Rosehip seed oil. In some such embodiments, the oil ingredient comprises Wheat germ oil. In some such embodiments, the oil ingredient comprises Meadowfoam seed. In some such embodiments, the oil ingredient comprises Castor oil. In some such embodiments, the essential oil ingredient comprises Lavender. In some such embodiments, the essential oil ingredient comprises Geranium. In some such embodiments, the essential oil ingredient comprises Frankinscense. In some such embodiments, the essential oil ingredient comprises Rose. In some such embodiments, the essential oil ingredient comprises Neroli. In some such embodiments, the essential oil ingredient comprises Sandalwood. In some such embodiments, the essential oil ingredient comprises Fennel. In some such embodiments, the essential oil ingredient comprises Patchouli. In some such embodiments, the essential oil ingredient comprises Chamomile. In some such embodiments, the essential oil ingredient comprises Rosemary. A skilled artisan will recognize that other coloring agents, homeopathic agents, preservatives, butters, oils and essential oils also may be used.

In yet another embodiment useful for protecting the skin against the harmful rays of the sun, Homeopathic Complex 5 is substituted for Homeopathic Complex 1. The cream foundation for preventing damage to the skin caused by the sun's harmful rays comprises Homeopathic Complex 5. In some such embodiments, the butter ingredient comprises Shea butter. In some such embodiments, the butter ingredient comprises Kokum butter. In some such embodiments, the oil is Grape seed oil. In some such embodiments, the oil ingredient comprises Avocado oil. In some such embodiments, the oil ingredient comprises Hazelnut oil. In some such embodiments, the oil ingredient comprises Almond oil. In some such embodiments, the oil ingredient comprises Pumpkin seed oil. In some such embodiments, the oil ingredient comprises Rosehip seed oil. In some such embodiments, the oil ingredient comprises Wheat germ oil. In some such embodiments, the oil ingredient comprises Meadowfoam seed. In some such embodiments, the oil ingredient comprises Castor oil. In some such embodiments, the essential oil ingredient comprises Lavender. In some such embodiments, the essential oil ingredient comprises Geranium. In some such embodiments, the essential oil ingredient comprises Frankinscense. In some such embodiments, the essential oil ingredient comprises Rose. In some such embodiments, the essential oil ingredient comprises Neroli. In some such embodiments, the essential oil ingredient comprises Sandalwood. In some such embodiments, the essential oil ingredient comprises Fennel. In some such embodiments, the essential oil ingredient comprises Patchouli. In some such embodiments, the essential oil ingredient comprises Chamomile. In some such embodiments, the essential oil ingredient comprises Rosemary. A skilled artisan will recognize that other homeopathic agents, coloring agents, preservatives, butters, oils and essential oils also may be used.

While the active ingredients may be used for any purpose for which any of the individual homeopathics are known to have utility, the active ingredients of the Homeopathic Complex of the foundation formulations are believed to work synergistically to achieve the results applicable to the Homeopathic Complex used. In general, the formulations strengthen the skin, rejuvenate and maintain the skin's well being, and promote overall health. The cream foundation of this example additionally is intended to add color to the skin and even out texture.

The cosmetic formulations of the present invention are delivered to the skin in order to best penetrate the body's defense mechanisms of the skin, and gain access to a cellular level where healing, rejuvenation, and maintenance begin. This one-step process is possible because the skin of the face contains oil and water. In addition, according to the present invention, active ingredients may be combined with inactive ingredients, including lipids and water, and applied in a two-step application process. Without being limited by theory, this two-step process, which allows penetration and delivery of the medicinal ingredients of the present invention through the stratum corneum, epidermis, dermis, and the subcutaneous tissue, and into the blood stream, provides effective and optimal delivery of the homeopathics and other medicinal ingredients of the cream foundation by providing access through the skin's layered absorption protection defenses. In this process, additional water is used to spread the lipids evenly over the stratum corneum; then, as the water either evaporates or penetrates the protein layer of the skin, the oils are left to penetrate the lipid layer.

Example 2

Face Powder

The face powder of the present invention is a homeopathic topical powder formulated for the delicate and highly susceptible skin of the face. The powder adheres to the skin creating an occlusion-like effect, thereby enhancing absorption. The powder is formulated to achieve the color, tint, and translucency desired. Powders of the present invention may be foundations, concealers, or colored and translucent setting powders, depending on the ratios of the ingredients. Foundations and concealers generally are prepared with lower amounts of serecite, while colored and translucent setting powders will contain more serecite.

In one embodiment, a face powder of the present invention is formulated in accordance with Table 10 below. All percentages are by weight.

TABLE 10

| Face Powder | |
| --- | --- |
| Ingredient | Percent (%) by Weight |
| Serecite | 0.00-100.0 |
| Zinc Oxide | 0.00-50.0 |
| Titanium Dioxide | 0.00-90.0 |
| Iron Oxide | 0.00-80.0 |
| Ultramarine Blue | 0.00-10.0 |
| Mica | 0.00-25.0 |
| Clay | 0.00-25.0 |

TABLE 10-continued

| Face Powder | |
| --- | --- |
| Ingredient | Percent (%) by Weight |
| Starch | 0.00-90.0 |
| Homeopathic Complex | 0.05-20.0 |

Ingredients other than the Homeopathic Complex are combined in a clean vessel to form a prebatched color cosmetic pigment mixture. The ingredients of the Homeopathic Complex are combined through the process of potenization. The liquid Homeopathic Complex is applied to the color cosmetic pigment mixture by a spraying technique.

In one embodiment of a loose powder foundation, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least clay. In another embodiment, the coloring agent comprises at least starch. In another embodiment, the coloring agent comprises at least zinc oxide. In another embodiment, the coloring agent comprises at least serecite.

In one embodiment of a loose powder concealer, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least serecite. In another embodiment, the coloring agent comprises at least clay. In another embodiment, the coloring agent comprises at least starch.

In one embodiment of a colored setting powder, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least serecite. In another embodiment, the coloring agent comprises at least clay. In another embodiment, the coloring agent comprises at least starch.

In one embodiment, Homeopathic Complex 1 is used for normal skin. In another embodiment, Homeopathic Complex 2 is used for problem skin. In another embodiment, Homeopathic Complex 3 is used for aging skin. In another embodiment, Homeopathic Complex 5 is used to prevent damage to the skin caused by the sun's harmful rays. A skilled artisan will recognize that other coloring agents and homeopathic agents may be used.

While the active ingredients may be used for any purpose for which any of the individual homeopathics are known to have utility, the active ingredients of the Homeopathic Complex in the powder formulations are believed to work synergistically to achieve the results applicable to the Homeopathic Complex used. In general the powder foundation formulations strengthen the skin, rejuvenate, promote health, and maintain the skin's well being. The powder foundation of this example is intended to add color to the skin, even out texture and hide imperfections.

Example 3

Blush

The blush of the present invention is a homeopathic topical powder formulated for the delicate and highly susceptible skin of the face. It adheres to the skin to create an occlusion-like effect and thereby enhances absorption of the active ingredients.

In one embodiment, a blush according to the present invention is formulated in accordance with Table 11 below. All percentages are by weight.

TABLE 11

| Blush | |
|---|---|
| Ingredient | Percent (%) by Weight |
| Mica | 0.01-5.0 |
| Iron Oxide | 0.01-90.0 |
| Titanium Dioxide | 10.0-99.8 |
| Ferric Ferrocyanide | 0.00-5.0 |
| Starch | 0.00-90.0 |
| Homeopathic Complex | 0.05-20.0 |

Ingredients other than the Homeopathic Complex are combined in a clean vessel to form a prebatched color cosmetic pigment mixture. The Homeopathic Complex is formulated by diluting and succussioning the Mother Tinctures of the desired ingredients in a process known as potenization. The liquid Homeopathic Complex is applied to the color cosmetic pigment mixture by a spraying technique.

In one embodiment of a colored blush according to the present invention, the coloring agent comprises at least mica. In another embodiment, the coloring agent comprises at least titanium dioxide. In another embodiment, the coloring agent comprises at least iron oxide. In another embodiment, the coloring agent comprises at least starch. In another embodiment, the coloring agent comprises at least ferric ferrocyanide.

In one embodiment, Homeopathic Complex 1 is used for normal skin. In another embodiment, Homeopathic Complex 2 is used for problem skin. In another embodiment, Homeopathic Complex 3 is used for aging skin. In another embodiment, Homeopathic Complex 5 is used to prevent damage to the skin caused by the sun's harmful rays. A skilled artisan will recognize that other coloring agents and homeopathic agents may be used.

While the active ingredients may be used for any purpose for which any of the individual homeopathics are known to have utility, the active ingredients of the Homeopathic Complex in the blush are believed to work synergistically to achieve the results applicable to the Homeopathic Complex used. In general the blush formulations strengthen the skin, rejuvinate, promote health, and maintain the skin's well being. The blush of this example is intended to add color to the skin, even out texture and hide imperfections.

Example 4

Eye Shadow

The eye shadow of the present invention is a homeopathic topical powder formulated for the delicate and highly susceptible skin of the eyelid. It may be shimmering or matte depending on the amount of mica or serecite present in the formulation.

In one embodiment, eye shadow is formulated in accordance with Table 12 below. All percentages are by weight.

TABLE 12

| Eye Shadow | |
|---|---|
| Ingredient | Percent (%) by Weight |
| Mica | 5.0-100.0 |
| Titanium Dioxide | 5.0-95.0 |
| Iron Oxide | 5.0-95.0 |
| Ultramarine Blue | 0.00-85.0 |
| Serecite | 0.0-30.0 |
| Starch | 0.00-90.0 |
| Clay | 0.00-25.0 |
| Homeopathic Complex | 0.05-20.0 |

Ingredients other than the Homeopathic Complex are combined in a clean vessel to form a prebatched color cosmetic pigment mixture. The ingredients of the Homeopathic Complex are combined through the process of potenization. The liquid Homeopathic Complex is applied to the color cosmetic pigment mixture by a spraying technique.

In one embodiment of a colored eyeshadow formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least serecite. In another embodiment, the coloring agent comprises at least clay. In another embodiment, the coloring agent comprises at least starch.

In one embodiment, Homeopathic Complex 1 is used for normal skin. In another embodiment, Homeopathic Complex 2 is used for problem skin. In another embodiment, Homeopathic Complex 3 is used for aging skin. In another embodiment, Homeopathic Complex 5 is used to prevent damage to the skin caused by the sun's harmful rays.

While the active ingredients may be used for any purpose for which any of the individual homeopathics are known to have utility, the active ingredients of the Homeopathic Complex in the eye shadow formulations work synergistically to achieve the results applicable to the Homeopathic Complex used. In general the eye shadow formulations strengthen the skin, rejuvinate, promote health, and maintain the skin's well being. The eye shadow of this example is intended to add color to the skin and accentuate to achieve a desired look. A skilled artisan will recognize that other coloring agents and homeopathic agents may be used.

Example 5

Eye Liner

The eye liner of the present invention is a homeopathic topical product formulated for the delicate and highly susceptible skin of the eye area.

In one embodiment, an eye liner is formulated in accordance with Table 13 below. All percentages are by weight.

TABLE 13

| Eye Liner | |
|---|---|
| Ingredient | Percent (%) by Weight |
| Wax | 23.8-35.7 |

TABLE 13-continued

Eye Liner

| Ingredient | Percent (%) by Weight |
|---|---|
| Oil | 37.0-52.6 |
| Coloring Agent | 10.2-19.6 |
| Homeopathic Complex | 0.5-20.0 |

Examples of waxes useful in the present invention include, but are not limited to, Beeswax, Candelilla Wax, Carnauba Wax, Emulsifying Wax, Lanolin Anhydrous, Jasmine Grandiflorum Wax, Jasmine Sambac Wax, Jojoba Wax Flakes, Mimosa Wax, Orange Peel Wax, and Rose Wax.

The eye liner of the present invention is prepared by first melting the wax. When completely melted, the wax is removed from heat. As the wax cools, the oils are slowly added while continuously stirring. Stirring is continued to avoid hardening until the solution is less than 120 degrees F. The coloring agents comprising the Homeopathic Complex then are added. The mixture is thoroughly mixed, poured into pencils, and allowed to cool and harden completely.

In one embodiment of a colored eye liner formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, Homeopathic Complex 1 is used for normal skin. In some such embodiments, the wax ingredient comprises beeswax. In some such embodiments the wax ingredient comprises carnauba. In some such embodiments, the oil ingredient comprises sesame oil. In some such embodiments, the oil ingredient comprises apricot kernel. In some such embodiments, the oil ingredient comprises wheat germ oil. In some such embodiments, the oil ingredient comprises castor oil.

In another embodiment, Homeopathic Complex 2 is used for problem skin. In some such embodiments; the wax comprises beeswax. In some such embodiment, the wax comprises carnauba. In some such embodiments, the oil ingredient comprises sesame oil. In some such embodiments, the oil ingredient comprises apricot kernel. In some such embodiments, the oil ingredient comprises wheat germ oil. In some such embodiments, the oil ingredient comprises castor oil.

In another embodiment, Homeopathic Complex 3 is used for aging skin. In some such embodiments; the wax comprises beeswax. In some such embodiments, the wax comprises carnauba. In some such embodiments, the oil ingredient comprises sesame. In some such embodiments, the oil ingredient comprises apricot kernel. In some such embodiments, the oil ingredient comprises wheat germ. In some such embodiments, the oil ingredient comprises castor oil.

In another embodiment, Homeopathic Complex 5 is used to prevent damage to the skin of the lip caused by the sun's harmful rays. In some such embodiments; the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil.

A skilled artisan will recognize that other homeopathic agents, coloring agents, waxes and oils may be used.

While the active ingredients may be used for any purpose for which any of the individual homeopathics are known to have utility, the active ingredients of the Homeopathic Complex in the eyeliner formulations are believed to work synergistically to achieve the results applicable to the Homeopathic Complex used. In general, the eyeliner formulations strengthen the skin, rejuvenate, promote healing, and maintain the skin's well being. The eyeliner of this example is intended to add color the skin and even out texture.

Example 6

Lip Liner

The lip liner of the present invention is a homeopathic topical product formulated for the delicate and highly susceptible skin of the lip area. The lip's inherent constitution and quality of thinness provides an optimal high rate of absorption, one of the highest rates on skin found on the human body, which makes the lip ideal for delivery of active substances to the body.

In one embodiment, a lip liner according to the present invention is formulated in accordance with Table 14 below.

TABLE 14

Lip Liner

| Ingredient | Percent (%) by Weight |
|---|---|
| Wax | 23.8-35.7 |
| Oil | 37.0-52.6 |
| Coloring Agent | 10.2-19.6 |
| Homeopathic Complex | 0.5-20.0 |

The lip liner of the present invention is made by first melting the wax. The wax is removed from the heat when it is melted completely. As the wax cools, the oil is slowly added while stirring continuously. The mixtures is stirred to avoid hardening until it is less than 120 degrees F., at which time the coloring agent containing the Homeopathic Complex is added and mixed completely. The mixture is poured into pencils and allowed to cool and harden completely.

In one embodiment of a colored lip liner formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ferric ferrocyanide. In another embodiment, the coloring agent comprises at least starch.

In one embodiment, Homeopathic Complex 1 is used for normal skin. In some such embodiments, the wax ingredient comprises beeswax. In some such embodiments the wax ingredient comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil.

In another embodiment, Homeopathic Complex 2 is used for problem skin. In some such embodiments; the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil.

In another embodiment, Homeopathic Complex 3 is used for aging skin. In some such embodiments; the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil.

In another embodiment, Homeopathic Complex 5 is used to prevent damage to the skin of the lip caused by the sun's harmful rays. In some such embodiments the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil.

A skilled artisan will recognize that other homeopathic agents, coloring agents, waxes and oils may be used.

While the active ingredients may be used for any purpose for which any of the individual homeopathics are known to have utility, the active ingredients of the Homeopathic Complex in the lip liner are believed to work synergistically to strengthen the skin, rejuvenate, and maintain the skin's well being. The lip liner of this example is intended to add color to the skin and define the lips. It promotes utilization by the body of inorganic minerals furthering the body's ability to heal, rejuvenate, and maintain itself. This in turn promotes the healthy, more youthful and vivacious appearance of the skin of the lip.

Example 7

Lipstick

The lipstick of the present invention is a homeopathic topical product formulated for the delicate and highly susceptible skin of the lip area. The lip's inherent constitution and quality of thinness provides an optimal high rate of absorption, one of the highest rates on skin found on the human body. This lipstick, which adheres to the skin, enhances the absorption of the active ingredients.

In one embodiment, the lipstick according to the present invention is formulated in a clean vessel in accordance with Table 15 below. All values are percentages by weight.

TABLE 15

| Lipstick | |
| --- | --- |
| Ingredient | Percent (%) by Weight |
| Wax | 17.1-27.2 |
| Oil | 39.6-70.7 |
| Essential Oil | 0.3-1.6 |
| Coloring Agent | 17.1-27.2 |
| Homeopathic Complex | 0.05-20.0 |

In one embodiment of a lipstick formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, Homeopathic Complex 1 is used for normal skin. In some such embodiments, the wax ingredient comprises beeswax. In some such embodiments, the wax ingredient comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In one embodiment, Homeopathic Complex 2 is used for problem skin. In some such embodiments, the wax ingredient comprises beeswax. In some such embodiments, the wax ingredient comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In one embodiment Homeopathic Complex 3 is used for aging skin. In some such embodiments, the wax ingredient comprises beeswax. In some such embodiments, the wax ingredient comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In another embodiment, Homeopathic Complex 5 is used to prevent damage to the skin of the lip caused by the sun's harmful rays. In some such embodiments, the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit. In some such embodiments, the essential oil ingredient comprises German Chamomile. In some such embodiments, the essential oil ingredient comprises Roman Chamomile. In some such embodiments, the essential oil ingredient comprises Cypress. In some such embodiments, the essential oil ingredient comprises Helichrysum. In some such embodiments, the essential oil ingredient comprises Jasmine.

A skilled artisan will recognize that other homeopathic agents, coloring agents, waxes, oils and essential oils may be used.

While the active ingredients may be used for any purpose for which any of the individual homeopathics are known to have utility, the active ingredients of the Homeopathic Complex in the lipstick are believed to work synergistically to strengthen the skin, rejuvenate, and maintain the skin's well being. The lipstick of the present invention is intended to add color to the skin and define the lips. It promotes utilization by the body of inorganic minerals furthering the body's ability to heal, rejuvenate, and maintain itself. This in turn promotes the healthy, more youthful and vivacious appearance of the skin of the lip.

Example 8

Lip Gloss

The lip gloss of the present invention is a homeopathic topical product formulated for the delicate and highly susceptible skin of the lip area. It adheres to the skin on the lip and thereby enhances the absorption of the active ingredients.

In one embodiment, the lip gloss according to the present invention is formulated in a clean vessel in accordance with Table 16. All values are percentages by weight.

TABLE 16

Lip Gloss

| Ingredient | Percent (%) by Weight |
| --- | --- |
| Butter | 8.4-16.4 |
| Oil | 44.5-79.5 |
| Essential Oil | 0.3-1.6 |
| Coloring Agent | 19.3-30.3 |
| Homeopathic Complex | 0.05-20.0 |

In one embodiment of a lip gloss formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, Homeopathic Complex 1 is used for normal skin. In some such embodiments, the butter ingredient comprises shea butter. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In one embodiment, Homeopathic Complex 2 is used for problem skin. In some such embodiments, the butter ingredient comprises shea butter. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In one embodiment, Homeopathic Complex 3 is used for aging skin. In some such embodiments, the butter ingredient comprises shea butter. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit.

In another embodiment, Homeopathic Complex 5 is used to prevent damage to the skin of the lip caused by the sun's harmful rays. In some such embodiments, the wax comprises beeswax. In some such embodiments, the wax comprises carnauba. In some such embodiments, the oil ingredient comprises sesame oil. In some such embodiments, the oil ingredient comprises apricot kernel oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises orange. In some such embodiments, the essential oil ingredient comprises tangerine. In some such embodiments, the essential oil ingredient comprises lemon. In some such embodiments, the essential oil ingredient comprises lime. In some such embodiments, the essential oil ingredient comprises grapefruit. In some such embodiments, the essential oil ingredient comprises German Chamomile. In some such embodiments, the essential oil ingredient comprises Roman Chamomile. In some such embodiments, the essential oil ingredient comprises Cypress. In some such embodiments, the essential oil ingredient comprises Helichrysum. In some such embodiments, the essential oil ingredient comprises Jasmine.

A skilled artisan will recognize that other homeopathic agents, coloring agents, butters, oils and essential oils may be used.

While the active ingredients may be used for any purpose for which any of the individual homeopathics are known to have utility, the active ingredients of the Homeopathic Complex in the lip gloss are believed to work synergistically to strengthen the skin, rejuvenate, and maintain the skin's well being. The lip liner of the present invention is intended to add color to the skin and define the lips. It promotes utilization by the body of inorganic minerals furthering the body's ability to heal, rejuvenate, and maintain itself. This in turn promotes the healthy, more youthful and vivacious appearance of the skin of the lip.

Example 9

Nail Polish

The Nail Polish of the present invention is a homeopathic topical nail coater for damaged nails. The absorption of the Homeopathic Complex through the nail is enhanced by the extended exposure time of the nail to the nail polish.

One embodiment of a nail polish formulation for the treatment of damaged nails comprises 0.05%-20.0% (by weight) of a Homeopathic Complex ingredient; a coloring agent; a water ingredient; a grain alcohol ingredient; a water miscible acrylic ingredient; a polyurethane ingredient; and a nonionic soap ingredient.

In one embodiment of a colored nail polish formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay.

In one embodiment for damaged nails, the Homeopathic Color Pigment Product comprises Homeopathic Complex 4, one embodiment of which is formulated in accordance with Table 7.

A skilled artisan will recognize that other coloring agents and homeopathic agents may be used.

While the active ingredients may be used for any purpose for which any of the individual homeopathics are known to have utility, the active ingredients of the Homeopathic Complex in the homeopathic nail polish are believed to work synergistically to strengthen, rejuvenate, and maintain the nail's well being. In addition the nail polish adds color to the nail and promotes absorption and utilization by the body of inorganic minerals furthering the body's ability to heal, rejuvenate, and maintain itself. This in turn promotes the healthy, more youthful and vivacious appearance of the nail.

Example 10

Sunscreen

The sunscreens of the present invention are formulated using the Homeopathic Color Pigment Products. Sunscreen Protection Factor will be calculated in accordance with 21 U.S.C. §52.70 which is expressly incorporated herein by reference.

In one embodiment, a Homeopathic Color Pigment Product is specifically formulated as a sunscreen for the delicate and highly susceptible skin of the face and body. One embodiment of a formulation of sunscreens is set forth in Table 18 below. All values are percentages by weight.

TABLE 18

| Sunscreen | |
|---|---|
| Ingredient | Percent by weight |
| Homeopathic Complex | 0.05-20.0 |
| Grain Alcohol | 1.1-3.7 |
| Gel | 12.9-23.9 |
| Butter | 8.2-16.2 |
| Oil* | 39.9-62.7 |
| Essential Oil | 0.18-1.40 |
| Preservative | 0.3-2.4 |
| Coloring Agent | 10.0-30.0 |
| Wax | 0.0-10.0 |

In one embodiment of a sunscreen formulated according to the present invention, the coloring agent comprises at least titanium dioxide. In another embodiment, the coloring agent comprises at least zinc oxide.

In one embodiment, Homeopathic Complex 5 is used to prevent damage to the skin caused by the sun's harmful rays. In some such embodiments, the gel ingredient comprises *aloe vera*. In some such embodiments, the butter ingredient comprises shea. In some such embodiments, the butter ingredient comprises aloe. In some such embodiments, the butter ingredient comprises kokum. In some such embodiments, the butter ingredient comprises avocado. In some such embodiments, the wax comprises beeswax. In some such embodiments, the wax comprises carnauba. In some such embodiments, the oil ingredient comprises sesame oil. In some such embodiments, the oil ingredient comprises coconut oil. In some such embodiments, the oil ingredient comprises sunflower. In some such embodiments, the oil ingredient comprises emu. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises German Chamomile. In some such embodiments, the essential oil ingredient comprises Roman Chamomile. In some such embodiments, the essential oil ingredient comprises Cypress. In some such embodiments, the essential oil ingredient comprises Helichrysum. In some such embodiments, the essential oil ingredient comprises Jasmine. In some such embodiments, the preservative is potassium sorbate.

A skilled artisan will recognize that other homeopathic agentx, coloring agents, gels, butters, waxes, oils, essential oils and preservatives may be used.

The sunscreen is applied according to standard usage practices by rubbing on the skin and by repeating application throughout periods of sun exposure so as to protect and provide a shielding effect against the sun and its damaging rays. While the active ingredients may be used for any purpose for which any of the individual homeopathics are known to have utility, the active ingredients of the Homeopathic Complex of the sunscreen product of the present invention are believed to work synergistically to protect the body from ill effects due to sun exposure, maintain the skin's well being and prevent excess fluid loss. The sunscreen of the present invention encourages the body to utilize inorganic minerals, including iron, potassium and sodium, furthering the body's ability to heal, rejuvenate, and maintain a healthy, more youthful and vivacious appearance.

Example 11

Eye Creams

The homeopathic eye creams of the present invention contain homeopathic topical solutions formulated for the delicate and highly susceptible skin around the eyes. They incorporate an inactive base of oils and butters, which facilitate absorption through the outer epidermis.

In some embodiments, active ingredients may be combined with inactive ingredients, including lipids and water, and applied in a two-step application process in order to penetrate the stratum corneum of the skin and thereby gain access at the cellular level where healing, rejuvenation and maintenance begin. Without being limited by theory, this two-step process provides effective and optimal delivery of the homeopathics and other medicinal ingredients. Water first is used to spread the lipids evenly over the stratum corneum. As the water either evaporates or penetrates the protein layer, the oils in the cream are left to penetrate the lipid part.

One embodiment of an eye cream formulation according to the present invention is set forth in Table 19. All values are percentages by weight.

TABLE 19

Eye Cream

| Ingredient | Percent by Weight |
| --- | --- |
| Homeopathic Complex | 0.05-20.0 |
| Grain Alcohol | 1.2-3.8 |
| Hydrosol | 2.4-5.8 |
| Butter | 22.4-43.6 |
| Oil | 32.3-66.4 |
| Essential Oil | 0.2-1.5 |
| Preservative | 0.3-1.6 |
| Coloring Agent | 5.0-30.0 |

In one embodiment of an eye cream formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, an eye cream for treating dark circles under the eyes comprises a hydrosol, a butter, an oil, an essential oil, and a Homeopathic Complex. In some such embodiments, the hydrosol ingredient comprises rose. In some such embodiments, the butter ingredient comprises cocoa butter. In some such embodiments, the butter ingredient comprises shea butter. In some such embodiments, the butter ingredient comprises kokum butter. In some such embodiments, the butter ingredient comprises sal butter. In some such embodiments, the oil ingredient comprises grape seed oil. In some such embodiments, the oil ingredient comprises almond oil. In some such embodiments, the oil ingredient comprises hazelnut oil. In some such embodiments, the oil ingredient comprises meadowfoam oil. In some such embodiments, the oil ingredient comprises pumpkin seed oil. In some such embodiments, the oil ingredient comprises rosehip seed oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises geranium. In some such embodiments, the essential oil ingredient comprises frankincense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary. In some such embodiments, the Homeopathic Complex comprises at least two of Abrotanum, *Baptisia tinctoria, Berberis vulgaris, Bryonia alba, Chelidonium rnajus, Cinchona officinalis-China, Echinacea augustitolia-Rudbeckia*, Kalium muriaticum, Kalium phosphoricum, Kalium sulphuricum, Mercurius cyanatus, Natrum muriaticum, Phosphorus, Phosphoricum acidum, Ptelea trifoliate, *Sabal serrulata* (saw palmetto), Silicea terra, Staphysagria, *Veratrum album; Carduus marianus*, and *Juniperus communis*.

In another embodiment, an eye cream for treating puffiness around the eyes comprises a hydrosol, a butter, an oil, an essential oil and a Homeopathic Complex. In some such embodiments, the hydrosol ingredient comprises rose. In some such embodiments, the butter ingredient comprises cocoa butter. In some such embodiments, the butter ingredient comprises shea butter. In some such embodiments, the butter ingredient comprises kokum butter. In some such embodiments, the butter ingredient comprises sal butter. In some such embodiments, the oil ingredient comprises grape seed oil. In some such embodiments, the oil ingredient comprises almond oil. In some such embodiments, the oil ingredient comprises hazelnut oil. In some such embodiments, the oil ingredient comprises meadowfoam seed oil. In some such embodiments, the oil ingredient comprises pumpkin seed oil. In some such embodiments, the oil ingredient comprises rosehip seed oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises geranium. In some such embodiments, the essential oil ingredient comprises frankincense. In some such embodiments, the essential oil ingredient comprises neroli. In some such embodiments, the essential oil ingredient comprises sandalwood. In some such embodiments, the essential oil ingredient comprises chamomile. In some such embodiments, the Homeopathic Complex comprises at least two of Ammonium benzoicum, *Apis mellifica*, Arsenicum album, *Belladonna, Cinchona officinalis-China, Echinacea augustitolia-Rudbeckia*, Ginseng quinque folium, Hepar sulphuris, Histaminum hydrochloricum, Kalium carbonicum, Kalium muriaticum, Kalium phosphoricum, Kalium sulphuricum, Natrium muriaticum, *Nux vomica*, Phosphorus, *Pulsatilla, Rhus toxicodendron, Sabal serrulata*, and Silicea terra.

In another embodiment, an eye cream for treating droopy eye lids comprises a hydrosol, a butter, an oil, an essential oil and a Homeopathic Complex. In some such embodiments, the hydrosol ingredient comprises rose. In some such embodiments, the butter ingredient comprises cocoa butter. In some such embodiments, the butter ingredient comprises shea butter. In some such embodiments, the butter ingredient comprises kokum butter. In some such embodiments, the butter ingredient comprises sal butter. In some such embodiments, the oil ingredient comprises grape seed oil. In some such embodiments, the oil ingredient comprises almond oil. In some such embodiments, the oil ingredient comprises hazelnut oil. In some such embodiments, the oil ingredient comprises meadowfoam seed oil. In some such embodiments, the oil ingredient comprises pumpkin seed oil. In some such embodiments, the oil ingredient comprises rosehip seed oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises geranium. In some such embodiments, the essential oil ingredient comprises frankincense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary. In some such embodiments, the Homeopathic Complex ingredient comprises at least two of *Aconitum napellus, Baptisia tinctoria, Berberis vulgaris, Cantharis vesicatoria, Carduus benedictus, Chelidonium majus, Cinchona officinalis-China, Echinacea augustitolia-Rudbeckia, Gelsenium sempervirens, Juniperus communis,* Kalium muriaticum, Kalium phosphoricum, Kalium sulphuricum, *Lachesis mutes, Lycopus virginicus,* Natrium arsenicosum, Natrum muriaticum, *Nux vomica, Phytolacca deca, Rhus toxicodendron,* Silicea terra and *Carduus marianus.*

In another embodiment, an anti-aging eye cream comprises a hydrosol, a butter, an oil, an essential oil and a Homeopathic Complex. In some such embodiments, the hydrosol ingredient comprises rose. In some such embodiments, the butter ingredient comprises cocoa butter. In some such embodiments, the butter ingredient comprises shea butter. In some such embodiments, the butter ingredient comprises kokum. In some such embodiments, the butter ingredient comprises sal butter. In some such embodiments, the oil ingredient comprises grape seed oil. In some such embodiments, the oil ingredient comprises almond oil. In some such embodiments, the oil ingredient comprises hazelnut oil. In some such embodiments, the oil ingredient comprises meadowfoam seed oil. In some such embodiments, the oil ingredient comprises pumpkin seed oil. In some such embodiments, the oil ingredient comprises rosehip seed oil. In some such embodiments, the oil ingredient comprises wheat germ oil. In some such embodiments, the oil ingredient comprises castor oil. In some such embodiments, the essential oil ingredient comprises lavender. In some such embodiments, the essential oil ingredient comprises geranium. In some such embodiments, the essential oil ingredient comprises frankincense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary. In some such embodiments, the Homeopathic Complex comprises at least two of Abrotanum, Argentum nitricum, Arsenicum album, Baryta carbonica, Cactus grandiflorus-*Selenicereus spinulosus, Chelidonium majus,* Cholesterlunum, *Conium maculatum,* Fluoricum acidum, Hepar sulphuris calcareum, *Hydrastis canadensis,* Kalium carbonicum, *Lilium tigrinum, Lycopodium clavatum,* Magnesia muriatica, Natrium muriaticum, *Podophyllum peltatum, Pulex irritans, Secale cornutum-Claviceps purpurea, Sepia officinalis,* and *Spigelia anthelmia* (pink root, annual worm grass).

A skilled artisan will recognize that other homeopathic agents, coloring agents, butters, oils, hydrosols, preservatives, and essential oils may be used.

While the active ingredients may be used for any purpose for which any of the individual homeopathics are known to have utility, the active ingredients of the Homeopathic Complex of the eye creams formulated according to the present invention are believed to work synergistically to strengthen, rejuvenate, and maintain the skin's well being. The creams promote absorption and utilization by the body of inorganic minerals, furthering the body's ability to heal, rejuvenate, and maintain itself, promote firmness to the skin around the eyes reducing sagging tissue, reduction in dark circles underneath the eyes, wrinkles due to aging or skin damage and/or swelling or puffiness. This in turn promotes the healthy, more youthful and vivacious appearance of the skin.

Example 12

Night Lotion

The night lotion of the present invention is a homeopathic topical cream formulated for the delicate and highly susceptible skin of the face. It incorporates an inactive base of oils, butters and hydrosols, which facilitate absorption through the outer epidermis.

In one embodiment, the night lotion of the present invention is mixed in a clean vessel in accordance with Table 20 below. All values are percent by weight.

TABLE 20

| Night Lotion | |
| --- | --- |
| Ingredient | Percent (%) by Weight |
| Homeopathic Complex | 0.05-20.0 |
| Grain Alcohol | 1.2-3.8 |
| Hydrosol and Other Liquids | 2.4-5.8 |
| Butter | 23.0-42.6 |
| Oil | 34.5-63.9 |
| Essential Oil | 0.2-1.5 |
| Preservative | 0.3-1.6 |
| Coloring Agent | 5.0-30.0 |

In one embodiment of a night lotion formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, a night lotion for normal skin comprises Homeopathic Complex 1. In some such embodiments, the liquid ingredient comprises lavender hydrosol. In some such embodiments, the butter ingredient comprises cocoa butter. In some such embodiments, the butter ingredient comprises shea butter. In some such embodiments, the oil ingredient comprises coconut oil. In some such embodiments, the oil ingredient comprises grape seed oil. In some such embodiments, the oil ingredient comprises almond oil. In some such embodiments, the essential oil ingredient comprises lavender. In some such embodiments, the essential oil ingredient comprises ylang ylang. In some such embodiments, the essential oil ingredient comprises chamomile. In some such embodiments, the essential oil ingredient comprises geranium. In some such embodiments, the essential oil ingredient comprises frankincense. In some such embodiments, the essential oil ingredient comprises rose.

In another embodiment, a night lotion for problem skin comprises Homeopathic Complex 2. In some such embodiments, the liquid ingredient comprises lavender hydrosol. In some such embodiments, the liquid ingredient comprises calendula lotion. In some such embodiments, the liquid ingredient comprises an infused herbal tea. In some such embodiments, the butter ingredient comprises shea butter. In some such embodiments, the oil ingredient comprises neem coconut oil. In some such embodiments, the oil ingredient comprises neem grape seed oil. In some such embodiments, the oil ingredient comprises tamanu oil. In some such embodiments, the oil ingredient comprises kukui nut oil. In some such embodiments, the essential oil ingredient comprises lavender. In some such embodiments, the essential oil ingredient comprises geranium. In some such embodiments, the essential oil ingredient comprises sandalwood. In some such embodiments, the essential oil ingredient comprises myrrh. In some such embodiments, the essential oil ingredient comprises frankincense. In some such embodiments, the essential oil ingredient comprises chamomile. In some such embodiments, the essential oil ingredient comprises rosehip seed.

In another embodiment, a night lotion for aging skin comprises Homeopathic Complex 3. In some such embodiments, the liquid ingredient comprises rose hydrosol. In some such embodiments, the butter ingredient comprises cocoa butter. In some such embodiments, the butter ingredient comprises shea butter. In some such embodiments, the butter ingredient comprises kokum butter. In some such embodiments, the butter ingredient comprises sal butter. In some such embodiments, the oil ingredient comprises grape seed oil. In some such embodiments, the oil ingredient comprises hazelnut oil. In some such embodiments, the oil ingredient comprises almond oil. In some such embodiments, the oil ingredient comprises pumpkin seed oil. In some such embodiments, the oil ingredient comprises rosehip seed oil. In some such embodiments, the oil ingredient comprises wheat germ oil. In some such embodiments, the oil ingredient comprises meadowfoam seed oil. In some such embodiments, the oil ingredient comprises castor oil. In some such embodiments, the essential oil ingredient comprises lavender. In some such embodiments, the essential oil ingredient comprises geranium. In some such embodiments, the essential oil ingredient comprises frankinscense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary.

A skilled artisan will recognize that other homeopathic agents, coloring agents, hydrosols, butters, oils, liquids, preservatives, and essential oils may be used.

While the active ingredients may be used for any purpose for which any of the individual homeopathics are known to have utility, the active ingredients of the Homeopathic Complex in the night lotion formulated according to the present invention are believed to work synergistically to strengthen and rejuvenate the skin, and to maintain the skin's well being. The formulations encourage the body to absorb and utilize inorganic minerals furthering the body's ability to heal, rejuvenate, and maintain. They also stimulate the epidermis to produce a healthy, more youthful and vivacious appearance through integrating the proprietary formula and application methodology to enhance the body's ability to absorb inorganic minerals. The inactive ingredients serve as an optimal carrier for the active ingredients.

Example 13

Facial Serum

The facial serum of the present invention is a homeopathic topical solution formulated for the delicate and highly susceptible skin of the face. This balm is formulated to incorporate an inactive base of oils to facilitate absorption through the outer epidermis.

In one embodiment, the facial serum of the present invention is mixed in a clean vessel in accordance with Table 21 below. All values are percent by weight.

TABLE 21

| Facial Serum | |
|---|---|
| Ingredient | Percent (%) by Weight |
| Oil | 67.6-105.0 |
| Homeopathic Complex | 0.05-20.0 |
| Grain Alcohol | 1.1-3.6 |
| Essential Oil | 0.4-2.5 |
| Preservative | 0.3-1.6 |
| Coloring Agent | 5.0-30.0 |

In one embodiment of a facial serum formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, a facial serum for normal skin comprises Homeopathic Complex 1. In some such embodiments, the oil ingredient comprises grape seed oil. In some such embodiments, the oil ingredient comprises almond oil. In some such embodiments, the oil ingredient comprises hazelnut oil. In some such embodiments, the essential oil ingredient comprises lavender. In some such embodiments, the essential oil ingredient comprises ylang ylang. In some such embodiments, the essential oil ingredient comprises chamomile. In some such embodiments, the essential oil ingredient comprises geranium. In some such embodiments, the essential oil ingredient comprises frankincense. In some such embodiments, the essential oil ingredient comprises rose.

In another embodiment, a facial serum for problem skin comprises Homeopathic Complex 2. In some such embodiments, the oil ingredient comprises neem coconut oil. In some such embodiments, the oil ingredient comprises neem grape seed oil. In some such embodiments, the oil ingredient comprises calendula rosehip seed oil. In some such embodiments, the oil ingredient comprises calendula oil. In some such embodiments, the oil ingredient comprises kukui nut oil. In some such embodiments, the essential oil ingredient comprises lavender. In some such embodiments, the essential oil ingredient comprises geranium. In some such embodiments, the essential oil ingredient comprises sandalwood. In some such embodiments, the essential oil ingredient comprises myrrh. In some such embodiments, the essential oil ingredient comprises frankincense. In some such embodiments, the essential oil ingredient comprises chamomile. In some such embodiments, the essential oil ingredient comprises rosehip seed.

In another embodiment, a facial serum for aging skin comprises Homeopathic Complex 3. In some such embodiments, the liquid ingredient comprises rose hydrosol. In some such embodiments, the butter ingredient comprises cocoa butter. In some such embodiments, the butter ingredient comprises shea butter. In some such embodiments, the butter ingredient comprises kokum butter. In some such embodiments, the butter ingredient comprises sal butter. In some such embodiments, the oil ingredient comprises grape seed oil. In some such embodiments, the oil ingredient comprises hazelnut oil. In some such embodiments, the oil ingredient comprises almond oil. In some such embodiments, the oil ingredient comprises rosehip seed oil. In some such embodiments, the oil ingredient comprises wheat germ oil. In some such embodiments, the oil ingredient comprises meadowfoam seed oil. In some such embodiments, the essential oil ingredient comprises lavender. In some such embodiments, the essential oil ingredient comprises geranium. In some such embodiments, the essential oil ingredient comprises frankinscense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary.

A skilled artisan will recognize that other homeopathic agents, coloring agents, preservatives, oils and essential oils may be used.

While the active ingredients may be used for any purpose for which any of the individual homeopathics are known to have utility, the active ingredients of the Homeopathic Complex in the facial serum formulated according to the present invention are believed to work synergistically to strengthen, rejuvenate, and maintain the skin's well being. The facial serum promotes absorption and utilization by the body of minerals furthering the body's ability to heal, rejuvenate, and maintain itself. This in turn promotes the healthy, more youthful and vivacious appearance of the skin.

Example 14

Facial Scrub

The Facial scrub of the present invention is a homeopathic scrub formulated for the delicate and highly susceptible skin of the face. It incorporates an inactive base of nourishing, exfoliating agents which facilitate absorption through the outer epidermis as they cleanse the pores.

In one embodiment, the facial scrub is mixed in a clean vessel in accordance with Table 22 below. All values are percent by weight.

TABLE 22

Facial Scrub

| Ingredient | Percent (%) by Weight |
|---|---|
| Humectant | 19.0-29.8 |
| Astringent | 8.1-16.2 |
| Oil | 23.6-12.7 |
| Homeopathic Complex | 0.05-15.0 |
| Grain Alcohol | 0.15-1.1 |
| Essential Oil | 0.2-1.6 |
| Exfoliator | 34.8-50.4 |
| Preservative | 0.37-1.6 |
| Coloring Agent | 5.0-30.0 |

In one embodiment of a facial scrub formulated according to the present invention, the coloring agent comprises at least mica. In another embodiment, the coloring agent comprises at least titanium dioxide. In another embodiment, the coloring agent comprises at least iron oxide. In another embodiment, the coloring agent comprises at least ultramarine blue. In another embodiment, the coloring agent comprises at least zinc oxide. In another embodiment, the coloring agent comprises at least ferric ferrocyanide. In another embodiment, the coloring agent comprises at least clay. In another embodiment, the coloring agent comprises at least serecite. In another embodiment, the coloring agent comprises at least starch.

In one embodiment, a facial scrub for normal skin comprises Homeopathic Complex 1. In some such embodiments, the humectant ingredient comprises glycerin. In some such embodiment, the humectant ingredient comprises honey. In some such embodiments, the astringent ingredient comprises witch hazel extract. In some such embodiments, the astringent ingredient comprises lavender hydrosol. In some such embodiments, the oil ingredient comprises almond oil. In some such embodiments, the oil ingredient comprises wheat germ oil. In some such embodiments, the exfoliator ingredient comprises orange peel. In some such embodiments, the exfoliator ingredient comprises almond flour. In some such embodiments, the exfoliator ingredient comprises milk powder. In some such embodiments, the essential oil ingredient comprises lavender. In some such embodiments, the essential oil ingredient comprises ylang ylang. In some such embodiments, the essential oil ingredient comprises chamomile. In some such embodiments, the essential oil ingredient comprises geranium. In some such embodiments, the essential oil ingredient comprises frankincense. In some such embodiments, the essential oil ingredient comprises rose.

In one embodiment, a facial scrub for problem skin comprises Homeopathic Complex 2. In some such embodiments, the humectant ingredient comprises glycerin. In some such embodiments, the humectant ingredient comprises honey. In some such embodiments, the astringent ingredient comprises witch hazel extract. In some such embodiments, the astringent ingredient comprises lavender hydrosol. In some such embodiments, the oil ingredient comprises almond oil. In some such embodiments, the oil ingredient comprises avocado oil. In some such embodiments, the oil ingredient comprises wheat germ oil. In some such embodiments, the exfoliator ingredient comprises orange peel. In some such embodiments, the exfoliator ingredient comprises Australian red reef clay. In some such embodiments, the exfoliator ingredient comprises Australian washed blue clay. In some such embodiments, the exfoliator ingredient comprises French yellow clay. In some such embodiments, the exfoliator ingredient comprises milk powder. In some such embodiments, the essential oil ingredient comprises lavender. In some such embodiments, the essential oil ingredient comprises geranium. In some such embodiments, the essential oil ingredient comprises sandalwood. In some such embodiments, the essential oil ingredient comprises myrrh. In some such embodiments, the essential oil ingredient comprises frankincense. In some such embodiments, the essential oil ingredient comprises chamomile. In some such embodiments, the essential oil ingredient comprises rosehip seed.

In one embodiment, a facial scrub for aging skin comprises Homeopathic Complex 3. In some such embodiments, the humectant ingredient comprises glycerin. In some such embodiments, the humectant ingredient comprises honey. In some such embodiments, the astringent ingredient comprises rose hydrosol. In some such embodiments, the astringent ingredient comprises lavender hydrosol. In some such embodiments, the oil ingredient comprises grape seed oil. In some such embodiments, the oil ingredient comprises hazelnut oil. In some such embodiments, the oil ingredient comprises almond oil. In some such embodiments, the oil ingredient comprises wheat germ oil. In some such embodiments, the exfoliator ingredient comprises lemon peel. In some such embodiments, the exfoliator ingredient comprises milk powder. In some such embodiments, the essential oil ingredient comprises lavender. In some such embodiments, the essential oil ingredient comprises geranium. In some such embodiments, the essential oil ingredient comprises frankincense. In some such embodiments, the essential oil ingredient comprises rose. In some such embodiments, the essential oil ingredient comprises neroli. In some such embodiments, the essential oil ingredient comprises sandalwood. In some such embodiments, the essential oil ingredient comprises fennel. In some such embodiments, the essential oil ingredient comprises patchouli. In some such embodiments, the essential oil ingredient comprises chamomile. In some such embodiments, the essential oil ingredient comprises rosemary seed.

A skilled artisan will recognize that other homeopathic agents, coloring agents, humectants, astringents, oils, exfoliators and essential oils may be used.

While the active ingredients may be used for any purpose for which any of the individual homeopathics are known to have utility, the active ingredients of the Homeopathic Complex in the facial scrubs are believed to work synergistically to strengthen, rejuvenate, and maintain the skin's well being. The facial scrub formulations of the present invention exfoliate the skin without removing natural moisturizers and encourage the body to absorb and utilize inorganic minerals, which in turn promotes the healthy, more youthful and vivacious appearance of the skin. When compared with commercially available facial scrubs, the facial scrub of the present invention left the subject's skin well moisturized, without feeling oily and did not cause dryness of the skin or breakouts to occur.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, ingredient, composition of matter, process, process step or steps, to the objective, spirit and scope of the present invention. All such modifications are intended to be within the scope of the claims appended hereto.

What is claimed is:

1. A delivery system to deliver topically to a subject a homeopathically effective amount of at least one Homeopathic Complex, the delivery system consisting essentially of:
   (a) a plurality of coloring agents comprising a plurality of particles having at least one surface; and
   (b) at least one hydrophilic Homeopathic Complex being complexed with at least one surface of the particles such that the coloring agent has the at least one Homeopathic Complex attached thereon, the Homeopathic Complex being defined by at least two homeopathic agents having an attenuation of at least 1X to provide a homeopathically effective amount,
   wherein the delivery system is a cosmetic formulation in the form of a make-up.

2. The delivery system according to claim 1 wherein the cosmetic formulation is in the form of a foundation make-up.

3. The delivery system according to claim 1 wherein the cosmetic formulation is in the form of a blush make-up.

4. The delivery system according to claim 1 wherein the cosmetic formulation is in the form of an eye shadow.

5. The delivery system according to claim 1, wherein the cosmetic formulation is in the form of at least one form selected from the group of an eye liner, a lip liner, a lipstick, and a lip gloss.

6. The delivery system according to claim 1 wherein the cosmetic formulation is in the form of a nail polish.

7. The delivery system according to claim 1 wherein the cosmetic formulation is in the form of a sunscreen.

8. The delivery system according to claim 1 wherein the cosmetic formulation is in the form of at least one form selected from the group consisting of a face cream, an eye cream, a lotion and a facial serum.

9. The delivery system according to claim 1 wherein the coloring agent is at least one coloring agent selected from the group consisting of mica, titanium dioxide, iron oxide, ferric ferrocyanide, ultramarine blue, clay, starch, talc, and zinc oxide.

10. The delivery system according to claim 1 wherein the at least one Homeopathic Complex comprises at least two homeopathic agents selected from the group consisting of Calcarea fluorica-Fluor spar, Calcarea phosphorica, Calcarea sulphurica, Ferrum phosphoricum, Kalium carbonicum, Kalium phosphoricum, Kalium sulphuricum, Magnesia phoshorica, Natrium muriaticum, Natrium Sulphuricurn, Sodium sulfide, Silicea terra, Azadirachta indica, Glycyrrhiza glabra, Carduus benedictus, Carduus marianus, Juniperus communis, and *Taraxacum officinale*.

11. The delivery system according to claim 10 wherein the Homeopathic Complex further comprises at least one homeopathic agent selected from the group consisting of *Centella asiatica, Curcuma longa, Eclipta alba, Emblica officinalis, Terminalia belerica* and *Terminalia chebula*.

12. The delivery system according to claim 1 wherein the at least one Homeopathic Complex comprises at least two homeopathic agents selected from the group consisting of *Antimonium crudum, Apis mellifica, Dulcamara, Graphites,*

*Kalium bromatum, Ledum palustre, Rhus toxicodendron, Berberis aquifolium-Mahonia, Lappa arctium*, and *Sarsaparilla officinalis*.

13. The delivery system according to claim 12 wherein the Homeopathic Complex further comprises at least one homeopathic agent selected from the group consisting of *Bovista lycoperdon, Candida albicans, Echinacea augustifolia-Rudbeckia, Fumaria officinalis, Hydrocotyle asiatica, Juglans regia, Taraxacum officinale, Rumex crispus*, and *Urtica urens*.

14. The delivery system according to claim 1 wherein the at least one Homeopathic Complex comprises at least two homeopathic agents selected from the group consisting of *Arsenicum album, Cactus grandiflorus-Selenicereus spinulosus, Chelidonium majus, Cholesteriunum, Kalium phosphoricum, Natrium muriaticum, Podophyllum peltatum*, Sepia officinal is, Silicea terra, and *Spigelia anthelmia*.

15. The delivery system according to claim 14 wherein the Homeopathic Complex further comprises at least one homeopathic agent selected from the group consisting of *Calcarea sulphurica, Conium maculatum, Ferrum phosphoricum, Hepar sulphuris calcareum, Hydrastis Canadensis, Kalium carbonicum, Kalium sulphuricum, Lilium tigrinum, Lycopodium clavatum, Magnesia muriatica*, and *Selenium Metallicum*.

16. The delivery system according to claim 1 wherein the at least one Homeopathic Complex comprises at least two homeopathic agents selected from the group consisting of Alumina, *Antimonium crudum*, Fluoricum acidum, Graphites, Nitricum acidum, *Sepia officinalis*, Silicea terra, Sulphuricum acidum, *Teucrium marum verum*, and *Thuja occidentalis*.

17. The delivery system according to claim 16 wherein the Homeopathic Complex further comprises at least one homeopathic agent selected from the group consisting of Arsenicum album, *Bryonia alba, Candida albicans, Dioscorea villosa, Dulcamara, Echinacea purpurea*, Hepar sulphuris calcareum, Kalium carbonicum, *Lachesis mutus, Lycopodium Clavatum*, Mezereum, Phosphorus, and Zincum metallicum.

18. The delivery system according to claim 1 wherein the at least one Homeopathic Complex comprises at least two homeopathic agents selected from the group consisting of *Aconitum napellus, Apis mellifica, Belladonna, Cantharis vesicatoria, Cinchona officinalis China*, Ferrum phosphoricum, Kalium carbonicum, Radium bromatum, *Sanguinaria canadensis*, and *Urtica urens*.

19. The delivery system according to claim 18 wherein the Homeopathic Complex further comprises at least one homeopathic agent selected from the group consisting of *Aceticum acidum*, Arsenicum album, *Baptisia tinctoria, Capsicum annuum*, Causticum, *Echinacea augustifolia, Euphorbium officinarum, Grindelia robusta, Hypericum perforatum*, Kalium carbonicum, Natrium muriaticum, *Nux vomica, Rhus toxicodendron, Secale comutum-Claviceps purpurea*, and Sulphur.

20. A Homeopathic Colored Pigment Product consisting essentially of (a) a plurality of coloring agents containing a plurality of particles having at least one surface; and (b) at least one hydrophilic Homeopathic Complex being complexed with the at least one surface of particles in the plurality of particles of the coloring agents to form a Homeopathic Color Complex,
   wherein the plurality of coloring agents are cosmetically acceptable coloring agents,
   wherein the Homeopathic Complex is defined by at least two homeopathic agents having an attenuation of at least 1X to provide a homeopathically effective amount, the Homeopathic Complex, and
   wherein the Homeopathic Colored Pigment Product is a cosmetic formulation in the form of a make-up.

21. The Homeopathic Colored Pigment Product according to claim 20 wherein the coloring agent is at least one coloring agent selected from the group consisting of mica, titanium dioxide, iron oxide, ferric ferrocyanide, ultramarine blue, clay, starch, and zinc oxide.

22. The Homeopathic Colored Pigment Product according to claim 20 wherein the at least one Homeopathic Complex comprises at least two homeopathic agents selected from the group consisting of Calcarea fluorica-Fluor spar, Calcarea phosphorica, Calcarea sulphurica, Ferrum phosphoricum, Kalium carbonicum, Kalium phosphoricum, Kalium sulphuricum, Magnesia phoshorica, Natrium muriaticum, Natrium Sulphuricum, Sodium sulfide, Silicea terra, *Azadirachta indica, Glycyrrhiza glabra, Carduus benedictus, Carduus marianus, Juniperus communis*, and *Taraxacum officinale*.

23. The Homeopathic Colored Pigment Product according to claim 22 wherein the Homeopathic Complex further comprises at least one homeopathic agent selected from the group consisting of *Centella asiatica, Curcuma longa, Eclipta alba, Emblica officinalis, Terminalia belerica* and *Terminalia chebula*.

24. The Homeopathic Colored Pigment Product according to claim 20 wherein the at least one Homeopathic Complex comprises at least two homeopathic agents selected from the group consisting of Antimonium crudum, *Apis mellifica, Dulcamara*, Graphites, Kalium bromatum, *Ledum palustre, Rhus toxicodendron, Berberis aquifolium-Mahonia, Lappa arctium*, and *Sarsaparilla officinalis*.

25. The Homeopathic Colored Pigment Product according to claim 24 wherein the at least one Homeopathic Complex further comprises at least one homeopathic agent selected from the group consisting of *Bovista lycoperdon, Candida albicans, Echinacea augustifolia-Rudbeckia, Fumaria officinalis, Hydrocotyle asiatica, Juglans regia, Taraxacum officinale, Rumex crispus*, and *Urtica urens*.

26. The Homeopathic Colored Pigment Product according to claim 20 wherein the at least one Homeopathic Complex comprises at least two homeopathic agents selected from the group consisting of *Arsenicum album, Cactus grandiflorus-Selenicereus spinulosus, Chelidonium majus*, Cholesteriunum, Kalium phosphoricum, Natrium muriaticum, *Podophyllum peltatum, Sepia officinalis*, Silicea terra, and Spigelia anthelmia.

27. The Homeopathic Colored Pigment Product according to claim 26 wherein the at least one Homeopathic Complex further comprises at least one homeopathic agent selected from the group consisting of Calcarea sulphurica, *Conium maculatum*, Ferrum phosphoricum, Hepar sulphuris calcareum, *Hydrastis Canadensis*, Kalium carbonicum, Kalium sulphuricum, *Lilium tigrinum, Lycopodium clavatum*, Magnesia muriatica, and Selenium Metallicum.

28. The Homeopathic Colored Pigment Product according to claim 20 wherein the at least one Homeopathic Complex comprises at least two homeopathic agents selected from the group consisting of Alumina, Antimonium crudum, Fluoricum acidum, Graphites, Nitricum acidum, *Sepia officinalis*, Silicea terra, Sulphuricum acidum, *Teucrium marum verum*, and *Thuja occidentalis*.

29. The Homeopathic Colored Pigment Product according to claim 28 wherein the Homeopathic Complex further comprises at least one homeopathic agent selected from the group consisting of Arsenicum album, *Bryonia alba, Candida albicans, Dioscorea villosa, Dulcamara, Echinacea purpurea*, Hepar sulphuris calcareum, Kalium carbonicum, *Lachesis mutus, Lycopodium clavatum*, Mezereum, Phosphorus, and Zincum metallicum.

30. The Homeopathic Colored Pigment Product according to claim 20 wherein the at least one Homeopathic Complex comprises at least two homeopathic agents selected from the group consisting of *Aconitum napellus, Apis mellifica, Belladonna, Cantharis vesicatoria , Cinchona officinalis-China*, Ferrum phosphoricum, Kalium carbonicum, Radium bromatum, *Sanguinaria Canadensis*, and *Urtica urens*.

31. The Homeopathic Colored Pigment Product according to claim 30 wherein the Homeopathic Complex further comprises at least one homeopathic agent selected from the group consisting of Aceticum acidum, Arsenicum album, *Baptisia tinctoria, Capsicum annuum*, Causticum, *Echinacea augustifolia, Euphorbium officinarum, Grindelia robusta, Hypericum perforatum*, Kalium carbonicum, Natrium muriaticum, *Nux vomica, Rhus toxicodendron, Secale comutum-Claviceps purpurea*, and Sulphur.

32. A method to deliver topically to a subject a cosmetic formulation comprising at least one Homeopathic Complex, the method comprising the steps of:
    (a) obtaining a plurality of coloring agents comprising a plurality of particles having at least one surface;
    (b) preparing the at least one hydrophilic Homeopathic Complex, wherein the Homeopathic Complex is defined by at least two homeopathic agents having an attenuation of at least 1X to provide a homeopathically effective amount;
    (c) depositing the at least one hydrophilic Homeopathic Complex onto the at least one surface of the coloring agents to form a Homeopathic Color Complex consisting essentially of (i) the plurality of coloring agents of (a); and (ii) at least one hydrophilic Homeopathic Complex being complexed with the at least one surface of particles in the plurality of particles of the coloring agents, such that the coloring agent has the at least one Homeopathic Complex attached thereon;
    (d) preparing a cosmetic formulation of the coloring agents having the homeopathically effective amount of the at least one Homeopathic Complex thereon, wherein the cosmetic formulation is in the form of make up; and
    (e) applying the cosmetic formulation to the skin of the subject, wherein the Homeopathic Complex is absorbed upon contact with the skin of the subject.

33. The method according to claim 32 wherein the coloring agent selected from the group consisting of mica, titanium dioxide, iron oxide, ferric ferrocyanide, ultramarine blue, a clay, starch, talc, and zinc oxide.

34. The method according to claim 32, wherein the cosmetic formulation is in the form of a foundation make-up.

35. The method according to claim 32, wherein the cosmetic formulation is in the form of a blush make-up.

36. The method according to claim 32, wherein the cosmetic formulation is in the form of an eye shadow.

37. The method according to claim 32, wherein the cosmetic formulation is in the form of at least one form selected from the group consisting of an eyeliner, a lip liner, a lipstick, and a lip gloss.

38. The method according to claim 32, wherein the cosmetic formulation is in the form of a nail polish.

39. The method according to claim 32, wherein the cosmetic formulation is in the form of a sunscreen.

40. The method according to claim 32, wherein the cosmetic formulation is in the form of at least one form selected from the group consisting of a face cream, an eye cream, a lotion and a facial serum.

41. The method according to claim 32, wherein the at least one Homeopathic Complex comprises at least two homeopathic agents selected from the group consisting of Calcarea fluorica-Fluor spar, Calcarea phosphorica, Calcarea sulphurica, Ferrum phosphoricum, Kalium carbonicum, Kalium phosphoricum, Kalium sulphuricum, Magnesia phoshorica, Natrium muriaticum, Natrium Sulphuricum, Sodium sulfide, Silicea terra, *Azadirachta indica, Glycyrrhiza glabra, Carduus benedictus, Carduus marianus, Juniperus communis*, and *Taraxacum officinale*.

42. The method according to claim 41, wherein the Homeopathic Complex further comprises at least one homeopathic agent selected from the group consisting of *Centella asiatica, Curcuma longa, Eclipta alba, Emblica officinalis, Terminalia belerica* and *Terminalia chebula*.

43. The method according to claim 32, wherein the at least one Homeopathic Complex comprises at least two homeopathic agents selected from the group consisting of *Antimonium crudum, Apis mellifica, Dulcamara*, Graphites, Kalium bromatum, *Ledum palustre, Rhus toxicodendron, Berberis aquifolium-Mahonia, Lappa arctium*, and *Sarsaparilla officinalis*.

44. The method according to claim 43, wherein the at least one Homeopathic Complex further comprises at least one homeopathic agent selected from the group consisting of *Bovista lycoperdon, Candida albicans, Echinacea augustifolia-Rudbeckia, Fumaria officinalis, Hydrocotyle asiatica, Juglans regia, Taraxacum officinale, Rumex crispus*, and *Urtica urens*.

45. The method according to claim 32, wherein the at least one Homeopathic Complex comprises at least two homeopathic agents selected from the group consisting of *Arsenicum album, Cactus grandiflorus-Selenicereus spinulosus, Chelidonium majus*, Cholesteriunum, Kalium phosphoricum, Natrium muriaticum, *Podophyllum peltatum, Sepia officinalis*, Silicea terra, and *Spigelia anthelmia*.

46. The method according to claim 45, wherein the at least one Homeopathic Complex the further comprises at least one homeopathic agent selected from the group consisting of Calcarea sulphurica, *Conium maculatum*, Ferrum phosphoricum, Hepar sulphuris calcareum, *Hydrastis Canadensis*, Kalium carbonicum, Kalium sulphuricum, *Lilium tigrinum, Lycopodium clavatum*, Magnesia muriatica , and Selenium Metallicum.

47. The method according to claim 32, wherein the at least one Homeopathic Complex comprises at least two homeopathic agents selected from the group consisting of Alumina, *Antimonium crudum*, Fluoricum acidum, Graphites, Nitricum acidum, *Sepia Officinalis*, Silicea terra, Sulphuricum acidum, *Teucrium marum verum*, and *Thuja occidentalis*.

48. The method according to claim 47, wherein the at least one Homeopathic Complex further comprises at least one homeopathic agent selected from the group consisting of Arsenicum album, *Bryonia alba, Candida albicans, Dioscorea villosa, Dulcamara, Echinacea urpurea*, Hepar sulphuris calcareum, Kalium carbonicum, *Lachesis mutus, Lycopodium clavatum*, Mezereum, Phosphorus, and Zincum metallicum.

49. The method according to claim 32, wherein the at least one Homeopathic Complex comprises at least two homeopathic agents selected from the group consisting of *Aconitum napellus, Apis mellifica, Belladonna, Cantharis vesicatoria, Cinchona officinalis*-China, Ferrum phosphoricum, Kalium carbonicum, Radium bromatum, *Sanguinaria canadensis*, and *Urtica urens*.

50. The method according to claim 49, wherein the at least one Homeopathic Complex further comprises at least one homeopathic agent selected from the group consisting of Aceticum acidum, Arsenicum album, *Baptisia tinctoria, Capsicum annuum,* Causticum, *Echinacea augustifolia, Euphorbium officinarum, Grindelia robusta, Hypericum perforatum,* Kalium carbonicum, Natrium muriaticum, *Nux vomica, Rhus toxicodendron, Secale cornutum Claviceps purpurea,* and Sulphur.

* * * * *